US009872516B2

(12) United States Patent
Gao et al.

(10) Patent No.: US 9,872,516 B2
(45) Date of Patent: *Jan. 23, 2018

(54) ORAL PRODUCT

(71) Applicant: ALTRIA CLIENT SERVICES LLC, Richmond, VA (US)

(72) Inventors: Feng Gao, Midlothian, VA (US); Frank Scott Atchley, Tarpon Springs, FL (US); Gregory James Griscik, Midlothian, VA (US); Christopher Joseph DiNovi, Ruther Glen, VA (US); Phillip M. Hulan, Midlothian, VA (US); Diane L. Gee, Chesterfield, VA (US); Jason Flora, Richmond, VA (US); Shuzhong Zhuang, Glen Allen, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/162,194

(22) Filed: Jan. 23, 2014

(65) Prior Publication Data

US 2014/0130814 A1  May 15, 2014

Related U.S. Application Data

(63) Continuation of application No. 13/744,930, filed on Jan. 18, 2013.
(Continued)

(51) Int. Cl.
*A24B 15/10* (2006.01)
*A24B 13/00* (2006.01)
*A24B 15/16* (2006.01)

(52) U.S. Cl.
CPC .............. *A24B 15/10* (2013.01); *A24B 13/00* (2013.01); *A24B 15/16* (2013.01)

(58) Field of Classification Search
CPC ....................................................... A24B 15/16
See application file for complete search history.

(56) References Cited

U.S. PATENT DOCUMENTS

| 1,977,059 | A | 10/1934 | Hatherell |
| 2,162,738 | A | 6/1939 | McCoy |

(Continued)

FOREIGN PATENT DOCUMENTS

| CN | 1054884 | 10/1991 |
| CN | 1064594 | 9/1992 |

(Continued)

OTHER PUBLICATIONS

Food Applications, International Fiber Corporation, http://buyersguide.supplysideshow.com/media/54/library/49964-313.pdf, 2010.*

(Continued)

*Primary Examiner* — Eric Yaary
(74) *Attorney, Agent, or Firm* — Fish & Richardson P.C.

(57) ABSTRACT

An oral product includes a body that is wholly receivable in an oral cavity. The body includes a mouth-stable polymer matrix, cellulosic fibers embedded in the mouth-stable polymer matrix, and nicotine or a derivative thereof dispersed in the mouth-stable polymer matrix. The oral product is adapted to release the nicotine or derivative thereof from the body when the body is received within the oral cavity and exposed to saliva.

63 Claims, 21 Drawing Sheets

Related U.S. Application Data

(60) Provisional application No. 61/588,873, filed on Jan. 20, 2012, provisional application No. 61/720,852, filed on Oct. 31, 2012.

(56) References Cited

U.S. PATENT DOCUMENTS

| | | | |
|---|---|---|---|
| 3,139,436 | A | 6/1964 | Bicking |
| 3,396,735 | A | 8/1968 | Von Bethmann et al. |
| 4,153,063 | A | 5/1979 | Roselius et al. |
| 4,241,090 | A | 12/1980 | Stroz et al. |
| 4,448,208 | A | 5/1984 | Friedrich et al. |
| 4,516,590 | A | 5/1985 | Teng |
| 4,528,993 | A | 7/1985 | Sensabaugh, Jr. et al. |
| 4,660,577 | A | 4/1987 | Sensabaugh et al. |
| 4,848,373 | A | 7/1989 | Lenkey |
| 4,983,405 | A | 1/1991 | Cherukuri et al. |
| 4,987,907 | A | 1/1991 | Townend |
| 5,144,967 | A | 9/1992 | Cartwright et al. |
| 5,372,149 | A | 12/1994 | Roth et al. |
| 5,417,229 | A | 5/1995 | Summers et al. |
| 5,487,792 | A | 1/1996 | King et al. |
| 5,656,284 | A | 8/1997 | Balkin |
| 5,906,811 | A | 5/1999 | Hersh |
| 6,110,495 | A | 8/2000 | Dam |
| 7,798,151 | B2 | 9/2010 | Krukonis et al. |
| 2004/0118422 | A1 | 6/2004 | Lundin et al. |
| 2004/0123873 | A1 | 7/2004 | Calandro et al. |
| 2004/0247669 | A1* | 12/2004 | Gin et al. ............ 424/468 |
| 2005/0046363 | A1 | 3/2005 | Yamamoto |
| 2005/0152971 | A1* | 7/2005 | Rinker et al. ............ 424/456 |
| 2005/0178398 | A1 | 8/2005 | Breslin et al. |
| 2005/0241658 | A1 | 11/2005 | Pera |
| 2005/0244521 | A1 | 11/2005 | Strickland et al. |
| 2006/0112965 | A1 | 6/2006 | Whalen |
| 2006/0185684 | A1 | 8/2006 | Albino et al. |
| 2006/0191548 | A1* | 8/2006 | Strickland et al. ............ 131/347 |
| 2007/0186942 | A1 | 8/2007 | Strickland et al. |
| 2007/0283974 | A1 | 12/2007 | May |
| 2008/0124283 | A1* | 5/2008 | Andersen ............ 424/48 |
| 2008/0209586 | A1 | 8/2008 | Nielsen et al. |
| 2008/0248017 | A1 | 10/2008 | Ron |
| 2008/0317911 | A1 | 12/2008 | Schleef et al. |
| 2009/0032040 | A1* | 2/2009 | Luzenberg, Jr. ............ 131/359 |
| 2009/0133703 | A1 | 5/2009 | Strickland et al. |
| 2009/0214445 | A1 | 8/2009 | Boghani et al. |
| 2009/0293889 | A1* | 12/2009 | Kumar et al. ............ 131/275 |
| 2009/0293895 | A1 | 12/2009 | Axelsson et al. |
| 2010/0061940 | A1* | 3/2010 | Axelsson et al. ............ 424/48 |
| 2010/0068270 | A1 | 3/2010 | Turchetta et al. |
| 2010/0163062 | A1 | 7/2010 | Atchley et al. |
| 2010/0170522 | A1 | 7/2010 | Sun et al. |
| 2010/0247594 | A1 | 9/2010 | Kuzma et al. |
| 2011/0139164 | A1* | 6/2011 | Mua et al. ............ 131/111 |
| 2011/0139166 | A1* | 6/2011 | Luzenberg, Jr. ............ 131/359 |
| 2011/0236442 | A1 | 9/2011 | Miser et al. |
| 2011/0274628 | A1* | 11/2011 | Borschke ............ 424/48 |
| 2012/0031415 | A1 | 2/2012 | Essen et al. |
| 2012/0318287 | A1 | 12/2012 | Andersen |
| 2013/0053603 | A1 | 2/2013 | Norström et al. |
| 2013/0186416 | A1 | 7/2013 | Gao et al. |
| 2013/0186417 | A1 | 7/2013 | Gao et al. |
| 2013/0186418 | A1 | 7/2013 | Gao et al. |
| 2013/0186419 | A1 | 7/2013 | Gao et al. |
| 2013/0189333 | A1 | 7/2013 | Gao et al. |

FOREIGN PATENT DOCUMENTS

| | | |
|---|---|---|
| CN | 1207251 | 2/1999 |
| CN | 1498080 | 5/2004 |
| CN | 1622758 A | 6/2005 |
| CN | 1903057 A | 1/2007 |
| CN | 1960648 A | 5/2007 |
| CN | 1961732 | 5/2007 |
| CN | 1997350 | 7/2007 |
| CN | 201156955 | 12/2008 |
| CN | 101861145 | 10/2010 |
| CN | 101877975 A | 11/2010 |
| CN | 102014654 A | 4/2011 |
| CN | 102300478 | 12/2011 |
| EA | 005421 | 2/2005 |
| EA | 005626 | 4/2005 |
| EP | 0 118 972 | 9/1984 |
| EP | 0 288 909 | 4/1988 |
| EP | 0279776 | 8/1988 |
| EP | 1 578 422 | 9/2005 |
| EP | 2 265 263 | 1/2009 |
| EP | 2 226 171 | 9/2010 |
| RU | 2291642 | 1/2007 |
| RU | 2342846 | 1/2009 |
| WO | WO 86/03102 | 6/1986 |
| WO | WO 92/20307 | 11/1992 |
| WO | WO 01/49124 | 7/2001 |
| WO | WO 02/076227 | 10/2002 |
| WO | WO 02/076230 | 10/2002 |
| WO | WO 2004/068965 | 8/2004 |
| WO | WO 2005/046363 | 5/2005 |
| WO | WO 2006/000232 | 1/2006 |
| WO | WO 2006/127772 | 11/2006 |
| WO | WO 2007/104573 | 9/2007 |
| WO | WO 2007/104574 | 9/2007 |
| WO | 2008/133982 | 11/2008 |
| WO | WO 2008/133982 | 11/2008 |
| WO | WO 2009/037319 | 3/2009 |
| WO | WO 2009/048522 | 4/2009 |
| WO | WO 2009/114034 | 9/2009 |
| WO | WO 2011/063338 | 5/2011 |
| WO | WO 2011/139943 | 11/2011 |
| WO | WO 2012/175085 | 12/2012 |

OTHER PUBLICATIONS

Chinese Office Action in Chinese Application No. 201210167508.1, mailed Dec. 4, 2013, 8 pages.
Chinese Office Action in Chinese Application No. 201210167234.6, mailed Jul. 19, 2013, 10 pages.
Chinese Office Action in Chinese Application No. 201210167332.X, mailed Dec. 4, 2013, 10 pages.
International Search Report and Written Opinion for PCT/US2013/022252 mailed Mar. 6, 2013, 12 pages.
International Search Report and Written Opinion for PCT/US2013/022204 mailed Dec. 16, 2013, 17 pages.
Krochta et al., "Edible and Biodegradable Polymer Films: Challenges and Opportunities," *Food Technology*, 1997, 51:61-74.
Tso, Tobacco Production, "Seed to Smoke," *Chemistry and Technology*, Blackwell Publishing, 1999, 1-31.
Chinese Office Action in Chinese Application No. 201210167206.4, mailed May 22, 2014, 11 pages.
Second Chinese Office Action in Chinese Application No. 201210167332.X, mailed May 30, 2014, 5 pages.
Second Chinese Office Action in Chinese Application No. 201210167508.1, mailed May 30, 2014, 2 pages (English Translation Only).
Chinese Office Action in Chinese Application No. 201210167166.3, mailed May 22, 2014, 4 pages.
Australian Office Action in Australian Application No. 2013204417, dated Dec. 5, 2014, 4 pages.
Chinese Office Action in Chinese Application No. 201210167508.1, mailed Oct. 10, 2014, 2 pages.
Fibersol, http://www.fibersol.com/products/fibersol-2/.
International Preliminary Report on Patentability for PCT/US2013/022204, mailed Jul. 22, 2014, 12 pages.
International Preliminary Report on Patentability for PCT/US2013/022252 mailed Jul. 22, 2014, 8 pages.
Chinese Office Action in Chinese Application No. 201380014374.2, dated Jun. 18, 2015, 12 pages (English Translation Only).
Chinese Office Action in Chinese Application No. 201380014374.2, dated Jan. 14, 2016, 14 pages (English Translation Only).
Dictionary of Chemistry and Chemical Technology, 2003, 5 pages (With English Translation).

(56) References Cited

OTHER PUBLICATIONS

Russian Office Action in Russian Application No. 2014134071, dated Jan. 26, 2017, 20 pages (with English translation).
European Notice of Opposition Against European Patent No. 2804897, dated Apr. 13, 2017, 22 pages.
Chinese Office Action in Chinese Application No. 201380014374.2, dated Jun. 2, 2016, 25 pages.
Extended European Search Report in European Application No. 16178530.8, dated Aug. 8, 2016, 7 pages.

* cited by examiner

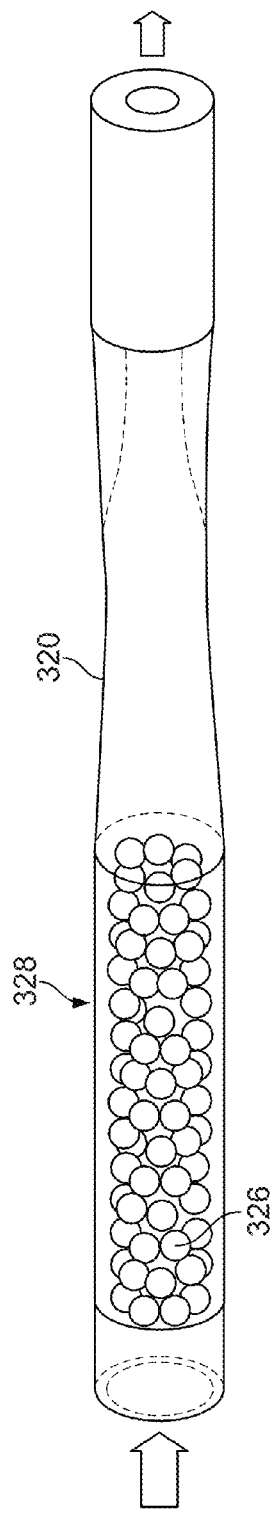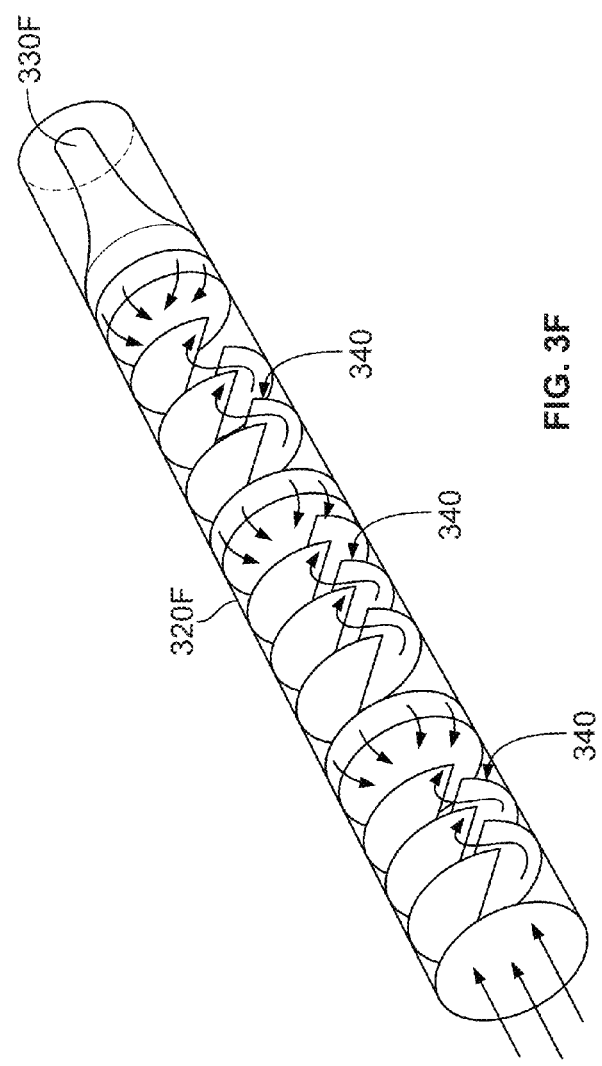
FIG. 3E
FIG. 3F

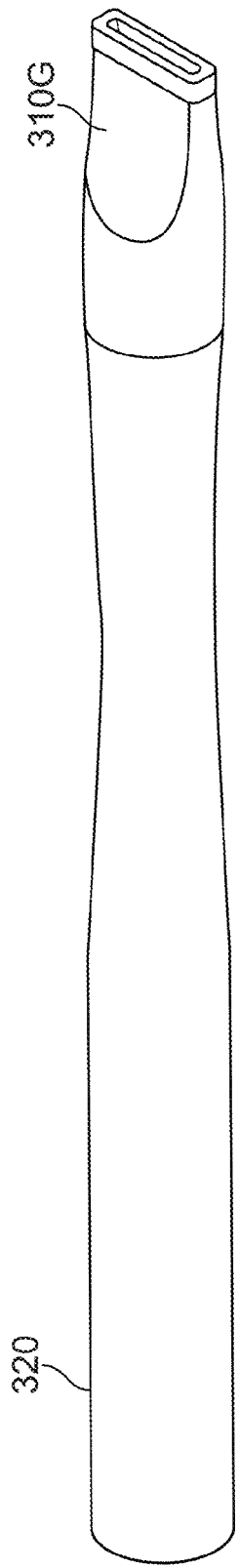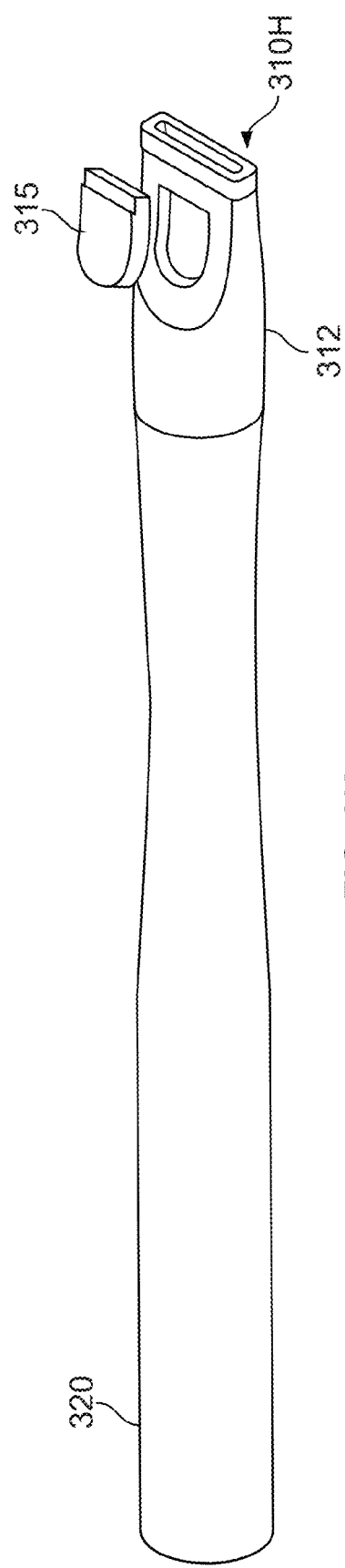
FIG. 3G
FIG. 3H

Product 7

Product 25

Fresh
Chewed
NRT Gum

Eraser

ORAL PRODUCT

CROSS-REFERENCE TO RELATED APPLICATIONS

This application is a continuation and claims priority to U.S. application Ser. No. 13/744,930 filed on Jan. 18, 2013 which claims priority to U.S. Provisional Application Ser. No. 61/588,873 filed Jan. 20, 2012 and U.S. Provisional Application Ser. No. 61/720,852 filed Oct. 31, 2012, both of which are incorporated by reference in their entirety.

TECHNICAL FIELD

This document relates to oral products including mouth-stable polymers and one or more additives.

BACKGROUND

Tobacco can be enjoyed by adult tobacco consumers in a variety of forms. Smoking tobacco is combusted and the aerosol either tasted or inhaled (e.g., in a cigarette, cigar, or pipe). Smokeless tobacco products are not combusted and include: chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat treated smokeless tobacco. Dry snuff is finely ground tobacco that is placed in the mouth or used nasally.

A growing number of governments are now implementing restrictions on smoking in public places, such as restaurants and transport facilities. In some countries, such as the United States, some workplaces are also covered by public restrictions. Smokeless products may also be banned by certain governments or workplaces.

Trans-buccal systems such as nicotine-containing chewing gum as well as transdermal nicotine delivery systems are well known in the art. These systems, however, do not consistently provide a suitable tobacco-like experience for some adult tobacco consumers.

SUMMARY

This specification describes an oral product that provides a satisfying tactile and/or flavor experience. In particular embodiments, the oral product can provide an extended additive release time. The oral product includes a body that is at least partially receivable in an oral cavity of an adult consumer. In some embodiments, the body includes a mouth-stable polymer matrix, cellulosic fibers embedded in the stable polymer matrix, and one or more additives dispersed in the body such that it is released when the body is received within the oral cavity and exposed to saliva.

The oral product, according to certain embodiments, includes nicotine or a derivative thereof. The oral product can provide a tobacco-like flavor experience and favorable tactile experience. Combinations of additives (e.g., sweeteners, flavorants, and nicotine) can be combined to provide a favorable tactile and flavor experience.

These and other embodiments can each optionally include one or more of the following features. In some embodiments, the oral product's body includes at least 10 weight percent of the mouth-stable polymer. The mouth-stable polymer matrix can include polyurethane, silicon polymer, polyester, polyacrylate, polyethylene, poly(styrene-ethylene-butylene-styrene) ("SEBS"), poly(styrene-butadiene-styrene) ("SBS"), poly(styrene-isoprene-styrene)("SIS"), and other similar thermoplastic elastomers, or any copolymer, mixture, or combination thereof. The oral product can also include a plasticizer dispersed in the mouth-stable polymer matrix. For example, the plasticizer can be propylene glycol, glycerin, vegetable oil, triglycerides, or a combination thereof. The oral product can also include a sweetener dispersed in the body. The sweetener can be saccharine, sucralose, aspartame, acesulfame potassium, or a combination thereof.

The oral product, according to certain embodiments, is substantially free of tobacco plant tissue. Nicotine added to the oral product can be either synthetic or derived from tobacco. In some embodiments, the oral product includes between 0.1 mg and 6 mg nicotine. The oral products can also include an additive selected from the group consisting of minerals, vitamins, dietary supplements, nutraceuticals, energizing agents, soothing agents, amino acids, chemsthetic agents, antioxidants, botanicals, teeth whitening agents, therapeutic agents, or a combination thereof. The nicotine and/or other additives can be absorbed into the cellulosic fibers and polymer matrix.

The oral product's body can have at least 10 weight percent cellulosic fibers. The cellulosic fibers can be derived from plant tissue. In some embodiments, the cellulosic fibers includes cellulose. The cellulosic fibers can further include lignin and/or lipids. The cellulosic fibers can be non-tobacco cellulosic fibers. For example, the cellulosic fibers can be selected from the following: sugar beet fiber, wood pulp fiber, cotton fiber, bran fiber, citrus pulp fiber, grass fiber, willow fiber, poplar fiber, and combinations thereof. The cellulosic fibers may also be chemically treated prior to use. For example, the cellulosic fibers can be CMC, HPMC, HPC, or other treated cellulosic material.

The oral product can include flavorants. The flavorants can be natural or artificial. Flavorants can be selected from the following: licorice, wintergreen, cherry and berry type flavorants, Drambuie, bourbon, scotch, whiskey, spearmint, peppermint, lavender, cinnamon, cardamon, *apium* graveolents, clove, cascarilla, nutmeg, sandalwood, bergamot, geranium, honey essence, rose oil, vanilla, lemon oil, orange oil, Japanese mint, *cassia*, caraway, cognac, jasmin, chamomile, menthol, ylang ylang, sage, fennel, pimenta, ginger, anise, coriander, coffee, mint oils from a species of the genus *Mentha*, cocoa, and combinations thereof. Synthetic flavorants can also be used. In certain embodiments, a combination of flavorants can be combined to imitate a tobacco flavor. The particular combination of flavorants can be selected from the flavorants that are generally recognized as safe ("GRAS"). Flavorants can also be included in the oral product as encapsulated flavorants.

The body of the oral product can have a variety of different shapes, some of which include disk, shield, rectangle, and square. According to certain embodiments, the body can have a length or width of between 5 mm and 25 mm and a thickness of between 1 mm and 10 mm.

The oral product's body can be compressible and springy. In some embodiments, the body has a compressibility @250 N of less than 95%, less than 90%, less than 85%, or less than 80%. In some embodiments, the body has a compressibility of @250 N of between 45% and 90%. The oral product's body can have a compressibility @425 N of less than 99%. For example, the body can have a compressibility @425 N of between 60% and 98%. The body can also have a percentage of springiness of at least 20%, at least 30%, at least 40%, at least 50%, at least 60%, at least 70%, or at least 75%. For example, the body can have a percentage of springiness of between 75% and 90%.

The oral product can also include an antioxidant. In some embodiments, the oral product includes between 0.01 weight percent and 5.0 weight percent antioxidant. Suitable antioxidants include ascorbyl palmitate, BHT, ascorbic acid, sodium ascorbate, monosterol citrate, tocopherols, propyl gallate, tertiary butylhydroquinone (TBHQ), butylated hydroxyanisole (BHA), Vitamin E, and derivatives thereof. The combination of antioxidant and nicotine can reduce the formation of nicotine-N-oxide.

The oral product can include a combination of soluble fibers and insoluble cellulosic fibers. In some embodiments, a ratio of soluble fiber to cellulosic fibers can be between 1:60 and 60:1. In some embodiments, the soluble fibers can include maltodextrin. In some embodiments, the soluble fibers comprise starch. The soluble fibers can be derived from corn. In general, another aspect of the subject matter described in this specification is methods of making and using the oral product. The methods of making the oral product can include the actions of extruding a mouth-stable polymer having cellulosic fibers and/or one or more additives dispersed therein.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIG. 3A-3J illustrate oral products having various rod, stick, or tube configurations.

DETAILED DESCRIPTION

Figure 1:
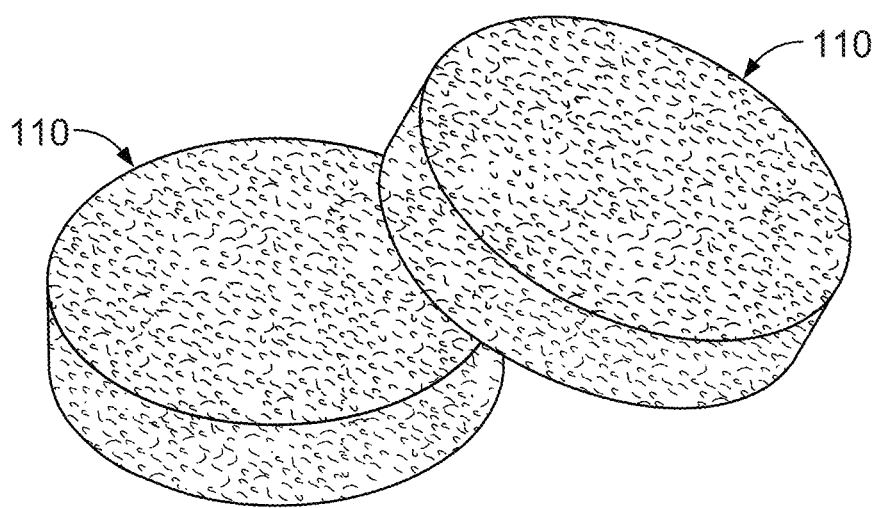
FIG. 1 is a perspective view of a pair of oral products.

The oral products described herein include a mouth-stable polymer matrix and one or more additives. The one or more additives can be dispersed in the mouth-stable polymer matrix such that the one or more additives are released from the oral product when the oral product is received within the oral cavity and exposed to saliva. The oral products described herein can provide a favorable additive release profile and tactile experience.

Suitable mouth-stable polymers include thermoplastic elastomers such as polyurethane. As used here, the term "mouth stable" means that the polymer does not appreciably dissolve or disintegrate when exposed to saliva within an oral cavity and at the normal human body temperature (e.g., about 98.6° F.) over a period of one hour. In addition to biostable polymers, mouth-stable polymers can include biodegradable polymers that breakdown over periods of days, weeks, months, and/or years, but do not appreciably break down when held in an oral cavity and exposed to saliva for a period of one hour. In some embodiments, the mouth-stable polymer is stable within an oral cavity and exposed to saliva at the normal human body temperature for a period of at least 6 hours, at least 12 hours, at least 24 hours, or at least 2 days. Accordingly, the oral products described herein can remain intact when placed within an oral cavity during a use period. After use, the mouth-stable polymer matrix can be removed from the oral cavity and discarded.

The mouth-stable polymer can have shape stability. In some cases, the oral product 110 can be chewed without significant and instantaneous permanent plastic deformation. As the oral product 100 is chewed, it can become more pliable and additional additives can become available for release into the oral cavity. Some embodiments of the oral product 110 can be adapted to remain non-sticky during and after use. After prolonged use, certain embodiments of the oral product 110 will expand and become flatter. The oral product, however, can retain the essence of its original shape.

One or more additives are included in the oral product and adapted to be released from the oral product when the oral product is placed in an oral cavity. The oral product, in some embodiments, includes nicotine. The oral product can include a combination of nicotine, sweeteners, and flavorants to mimic the flavor profile and tactile experience of certain tobacco products (e.g., a pouched smokeless tobacco product).

In some embodiments, a nicotine-containing oral product can be substantially free of tobacco plant tissue. As used herein, the term "tobacco plant tissue" refers to processed or non-processed cellulosic parts (e.g., leaves, stems) of a member of the genus *Nicotiana*, but does not include extracts of tobacco (e.g., tobacco-derived nicotine). For example, an oral product can include one or more organoleptic components extracted from raw or processed tobacco, yet be substantially free of tobacco plant tissue.

In addition to additives, sweeteners, and flavorants, the oral product can also include fibers, fillers, plasticizers, and/or processing aids. Fibers can help provide access to the additives, sweeteners, and/or flavorants. As will be discussed below, fibers can provide channels for additives, sweeteners, and/or flavorants to leach out of the mouth-stable polymer matrix. The fiber-polymer matrix can absorb one or more additives and provide a pathway for one or more additives to be released from the oral product. The fiber-polymer matrix can be porous. In some embodiments, the fiber-polymer matrix can have a plurality of pores having a pore diameter of between 40 microns and 60 microns and a plurality of pores having a pore diameter of between 1 micron and 10 microns. During use, saliva can be absorbed into the fiber-polymer matrix to release the additives, sweeteners, and/or flavorants. The absorbed saliva can enter the pores and/or cause the fibers to expand, which can facilitate further release of additives, sweeteners, and/or flavorants.

Mechanical action (e.g., chewing) of the oral product can facilitate the release of the additives, sweeteners, and/or flavorants.

Fillers can also be included in the mouth-stable polymer matrix to alter the texture or pliability of the oral product. The mouth-stable polymer matrix can also include plasticizers, which can increase the softness of the oral product. Processing aids can also be present in the oral product and be used to facilitate shaping processes.

Oral Product Shapes and Packaging

FIG. 1 depicts an example of an oral product 110. The oral product 110 has a disk shape. For example, the oral product 110 can have a diameter of about 12 mm and a thickness of about 2.5 mm.

Figure 2A:
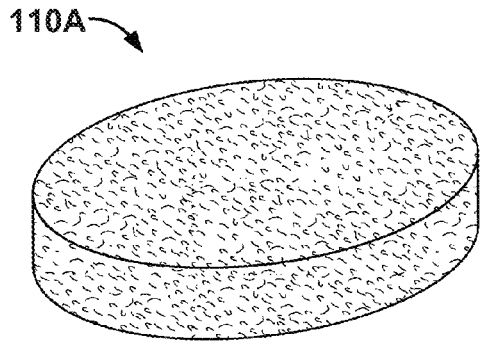
FIGS. 2A-2O illustrate various exemplary shapes of oral products.
Figure 2B:
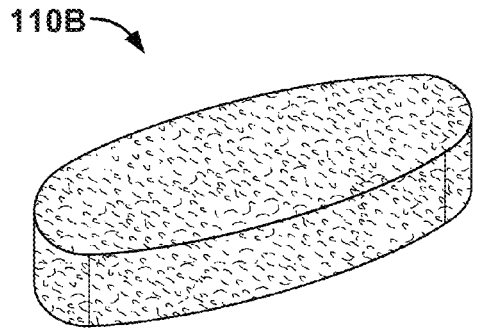
Figure 2C:
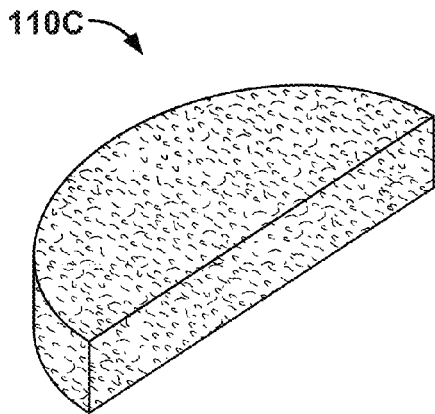
Figure 2D:
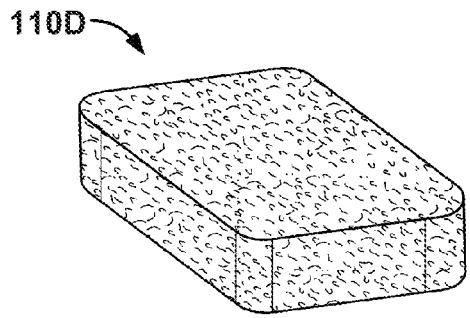
Figure 2E:
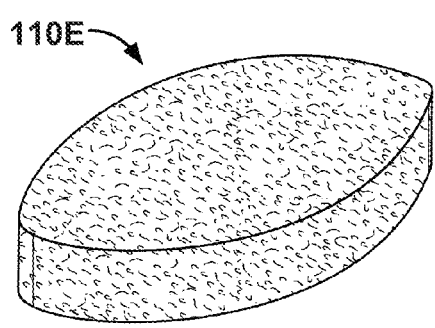
Figure 2F:
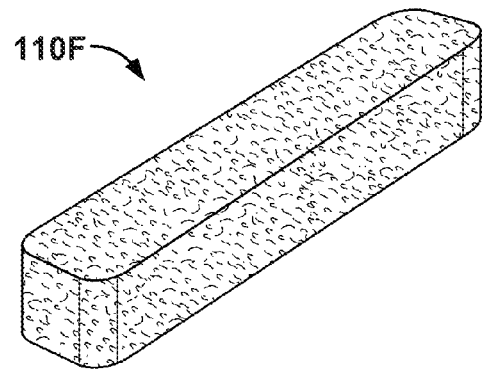
Figure 2G:
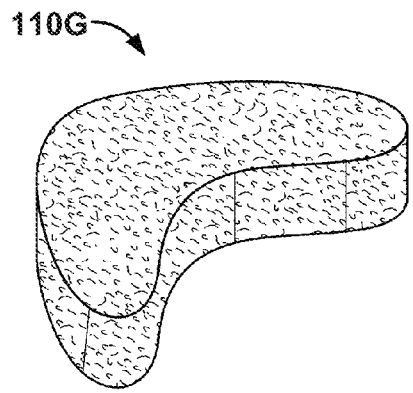
Figure 2H:
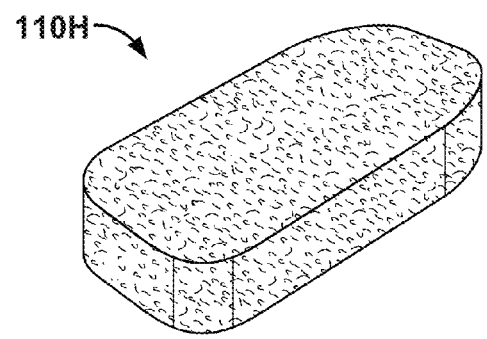
Figure 2I:
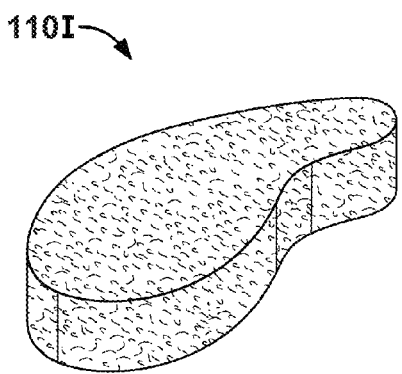
Figure 2J:
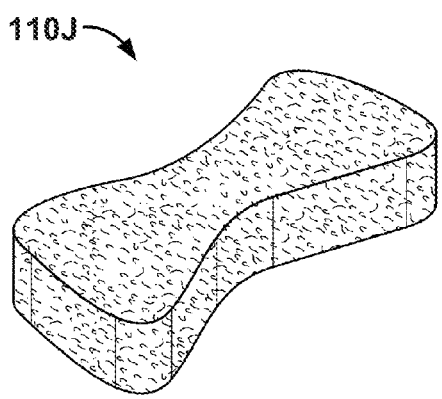
Figure 2K:
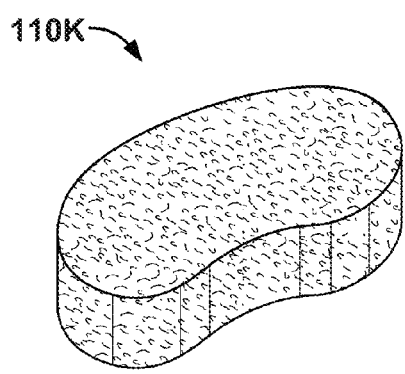
Figure 2L:
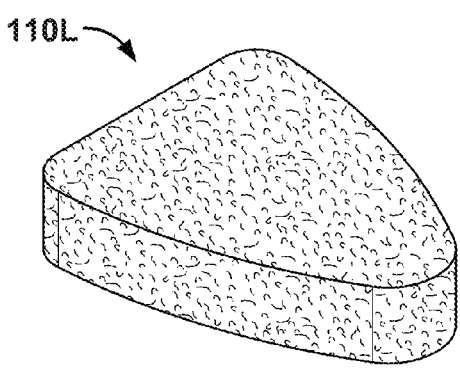
Figure 2M:
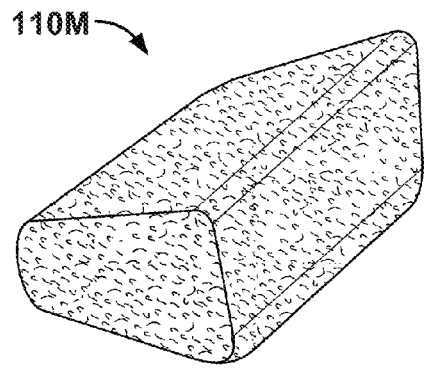
Figure 2N:
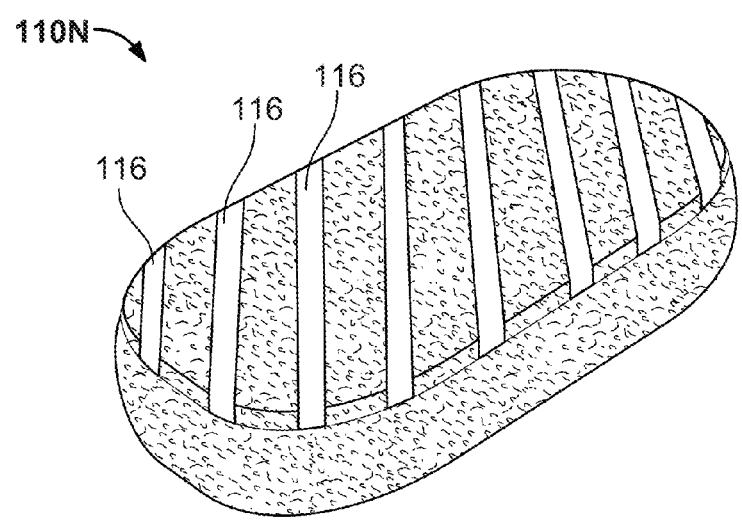

Referring now to FIGS. 2A-2N, the oral product 110 can be molded into any desired shape. For example, referring to FIGS. 2A-2L, the oral product 110A-L can be formed in a shape that promotes improved oral positioning in the oral cavity, improved packaging characteristics, or both. In some circumstances, the oral product 110A-L can be configured to be: (A) an elliptical-shaped oral product 110A; (B) an elongated elliptical-shaped oral product 110B; (C) semi-circular oral product 110C; (D) square or rectangular-shaped oral product 110D; (E) football-shaped oral product 110E; (F) elongated rectangular-shaped oral product 110F; (G) boomerang-shaped oral product 110G; (H) rounded-edge rectangular-shaped oral product 110H; (I) teardrop- or comma-shaped oral product 110I; (J) bowtie-shaped oral product 110J; (K) peanut-shaped oral product 110K; and (L) shield-shaped oral product. Alternatively, the oral product can have different thicknesses or dimensionality, such that a beveled article (e.g., a wedge) is produced (see, for example, product 110M depicted in FIG. 2M) or a hemi-spherical shape is produced. In some embodiments, the oral product has a shield shape.

In addition or in the alternative to flavorants being included within the mouth-stable polymer matrix, flavorants can be included on an exterior of the oral product 110. For example, referring to FIG. 2N some embodiments of an oral product 110N can be equipped with flavor strips 116.

Figure 2O:
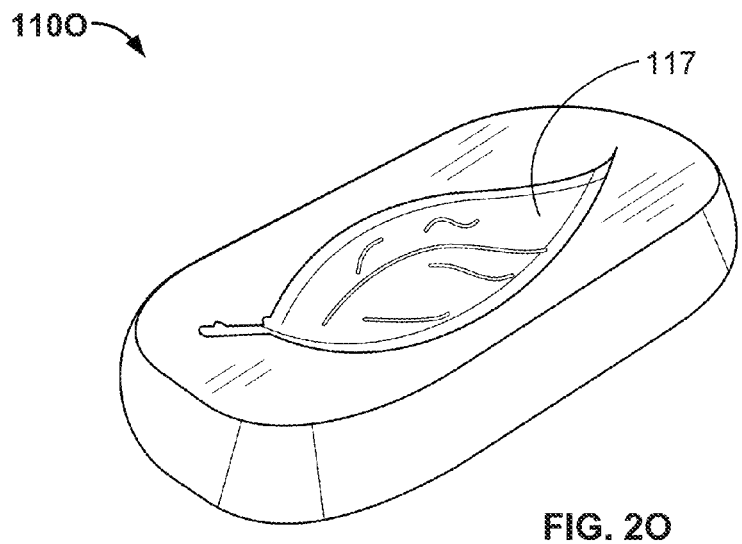

Referring to FIG. 2O, particular embodiments of the oral product 110 can be embossed or stamped with a design (e.g., a logo, an image, or the like). For example, the oral product 110O can be embossed or stamped with any type of design 117 including, but not limited to, a trademark, a product name, or any type of image. The design 117 can be formed directly into the oral product, arranged along the exterior of the product 110O. The design 117 can also be embossed or stamped into those embodiments with a dissolvable film 116 applied thereto.

In some embodiments, the oral product 110 or products 110A-O can be wrapped or coated in an edible or dissolvable film, which may be opaque, substantially transparent, or translucent. The dissolvable film can readily dissipate when the oral product 110 is placed in an oral cavity. In some embodiments, the oral product 110 can be coated with a mouth-stable material. Exemplary coating materials include Beeswax, gelatin, acetylated monoglyceride, starch (e.g., native potato starch, high amylose starch, hydroxypropylated potato starch), Zein, Shellac, ethyl cellulose, methylcellulose, hydroxypropyl methylcellulose, carboxymethyl cellulose, and combinations thereof. For example, a coating can include a combination of gelatin and methylcellulose. In some embodiments, a coating material can include a plasticizer. In some case, a coating can include a colorant, a flavorant, and/or a one or more of the additives discussed above. For example, a coating can include nicotine to provide a user with an initial nicotine burst. In some cases, the matrix of mouth-stable polymer 120 can have surfaces roughened to improve the adherence of a coating. In some cases, a coating can provide a glossy or semi-glossy appearance, a smooth surface, and/or an appealing visual aesthetic (e.g., a nice color). In some embodiments, the coating (e.g., a beeswax, Zein, acetylated monoglyceride, and/or hydroxypropylated potato starch coating) can provide soft mouth feel. In some embodiments, the coating (e.g., a methylcellulose, hydroxypropyl methylcellulose, carboxymethyl cellulose, ethyl cellulose, and/or gelatin coating) can provide a hard outer coating.

One or more oral products 110 can be packaged in a variety of conventional and non-conventional manners. For example, a plurality of oral products 110 can be packaged in a container having a lid. In other embodiments, a plurality of oral products 110 can be stacked and packaged in a paper, plastic, and/or aluminum foil tube. The packaging can have a child-resistant lid.

Figure 3A:
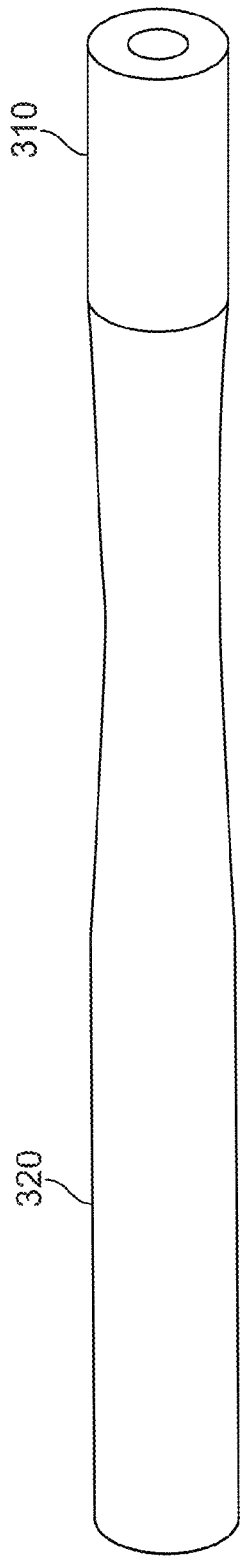
Figure 3B:
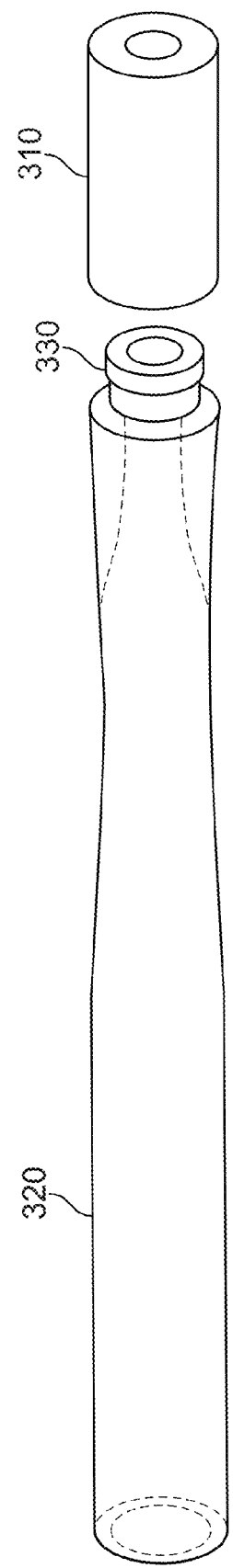

The oral product 110 can also include additional elements. In some embodiments, a mouth-stable polymer matrix including nicotine or a derivative thereof can be attached to a rod, tube, or stick. For example, FIGS. 3A-3J illustrate tubes attached to a mouth-stable polymer matrix tips. FIG. 3A depicts an embodiment of an oral product having a tip piece 310 and a tube piece 320. The tip piece 310 can include the mouth-stable polymer matrix having fibers and/or one or more additives within the polymer matrix. The tip piece 310 can be sized and shaped to be at least partially received in an oral cavity. The tube piece 320 can be made of any conventional polymer. During use the tube piece 320 can act as holder for the tip piece 310. The tube piece 320 and the tip piece 310 can be attached by a snap-fit attachment feature 330, as shown in FIG. 3B.

Figure 3C:
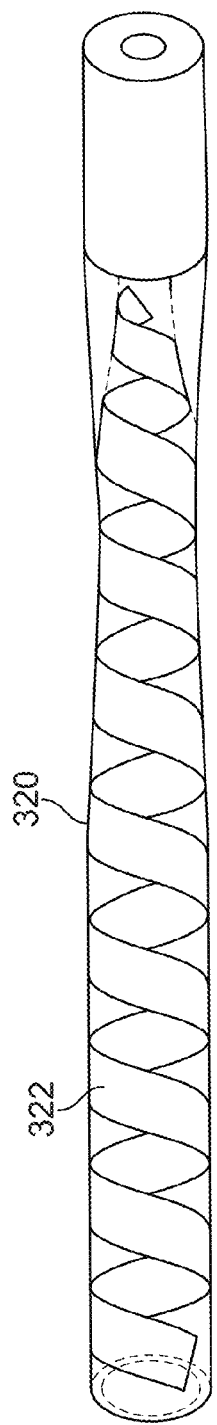
Figure 3D:
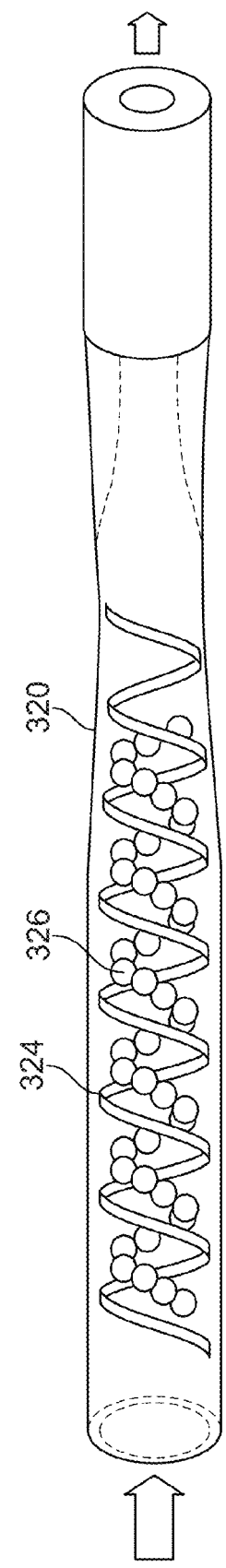

The tube piece 320 can be reusable. For example, multiple tip pieces 310 can be packaged with a single tube piece 320 and a user can switch off the tip pieces 310. In other embodiments, the tube pieces 320 can be intended for a single use. In some embodiments, the tube pieces 320 can include flavorants within the tube. The flavorants can be adapted to be released when air is drawn through the tube 320. For example, FIG. 3C depicts a tube including a flavor ribbon 322. FIG. 3D depicts a tube 320 including a flavor strip 324 and a plurality of flavor beads 326. FIG. 3E depicts a tube 320 including a compressed mass 328 of flavor beads 326. In some embodiments, the inside of the tube can have structure adapted to alter the flow pattern of air drawn into the tube. For example, FIG. 3F depicts a tube 320F having a series of steps and constrictions 340 adapted to alter the flow pattern of air drawn into the tube. FIG. 3F also depicts an alternative connection feature 330F.

FIG. 3G depicts an embodiment having a recorder-like shape. As shown, a tip piece 310G is connected to the contoured tube piece 320. For example, the recorder-shaped tip 310G can be composed of a mouth-stable polymer matrix that includes cellulosic fibers, nicotine, one or more sweeteners, and one or more flavorants. As shown, the tip piece 310G is sized and shaped to be at least partially received within an adult's oral cavity.

Figure 3I:
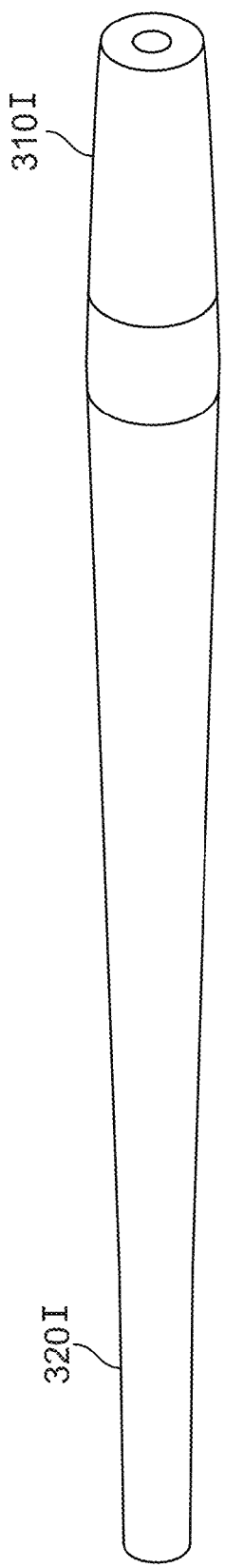
Figure 3J:
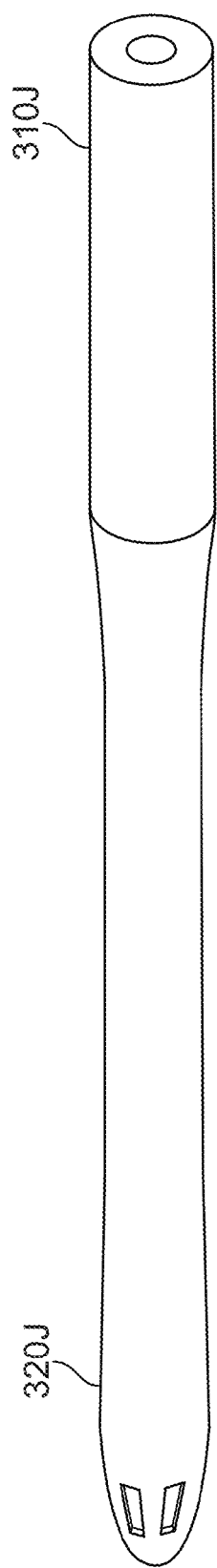

FIG. 3H depicts a similarly shaped oral product having a plastic recorder-shaped tip 310H that includes a reusable plastic part 312 and a mouth-stable polymer matrix part 315. FIGS. 3I and 3J depict embodiments having alternatively shaped tip pieces 310I and 310J. FIG. 3I depicts an embodiment having a tapered tube 320I. FIG. 3J depicts an embodiment having vent holes at the non-tip end of the tube piece 320J.

In some embodiments, a system or kit of different tubes and rods and/or different tips can be packaged together, each having the same type of attachment features. Embodiments having each of the combinations of tips and tubes or rods shown in FIGS. 3A-3J are contemplated.

Oral Product Properties

The oral product 110 can provide a favorable tactile experience (e.g., mouth feel). The oral product 110 can also retain its shape during processing, shipping, handling, and optionally use. As noted above, the oral product 110 includes a mouth-stable polymer matrix that does not appreciably dissolve or disintegrate when placed in an oral cavity and exposed to saliva. In some embodiments, the oral product 110 can have an elasticity allowing an adult consumer to work the product within the mouth. In some embodiments, the oral product 110 has at least some shape memory and thus can return to shape after being squeezed between teeth in an oral cavity. Working of the oral product 110 within the oral cavity can accelerate the release of the additives, sweeteners, and/or flavorants within the mouth-stable polymer matrix.

During use, the oral product 110 can absorb saliva into the polymer-fiber matrix. The saliva can cause the polymer-fiber matrix to swell, which can further increase access to different sections of the polymer-fiber matrix. Physical activity, such as chewing of the product in the mouth, can also accelerate the polymer-matrix swelling and therefore the release of additives. As the product is chewed, saliva can access different sections of the polymer-fiber matrix. The mouth-stable polymer can have shape stability. In some cases, the oral product 110 can be chewed without significant and instantaneous permanent plastic deformation (such as that experienced by a chewing gum when chewed). As the oral product 100 is chewed, it can become more pliable and additional additives can become available for release into the oral cavity. Some embodiments of the oral product 110 can be adapted to remain non-sticky during and after use. After prolonged use, certain embodiments of the oral product 110 will expand and become flatter. The oral product, however, can retain the essence of its original shape. The amount of deformation will depend on the duration of use and an amount of mouth force used. As the product is used, it can increase in both weight and volume, due to the swelling. Simulated chewing tests using artificial saliva show a weight increases ranging from 4% to 75% depending on the selection of experimental parameters. With greater the physical manipulation, the oral product 110 will have a greater amount of swelling and thus have a larger weight gain. In certain embodiments, the oral product 110 will have an increase in weight of between 4 and 75 percent when chewed by an adult consumer for 30 minutes.

One way of characterizing the properties of the oral product is by measuring the compressibility and springiness of the product. The compressibility can be calculated as a percentage of reduction in thickness of the sample when the sample is compressed with a standardized probe with a particular force. As used herein, the term "compression @250 N test" defines a test of a sample where the sample is placed on a flat stationary surface and twice compressed with a 10 mm-diameter-sphere-tipped probe with a force of 250 N with a hold time of 30 seconds between compressions. The "percentage of compression @250 N" is the maximum amount of reduction in thickness of the sample during the compression @250 N test. For example, if a 3 mm thick sample is compressed to a minimum thickness of 1.5 mm during either of the two compressions, the sample is said to have a 50% compression @250 N. As used herein, the term "compression @425 N test" defines a test of a sample where the sample is placed on a flat stationary surface and twice compressed with a 10 mm-diameter-sphere-tipped probe with a force of 425 N with a hold time of 30 seconds between compressions. For comparison, a normal human bite force is typically between 400 and 500 N.

Figure 9A:
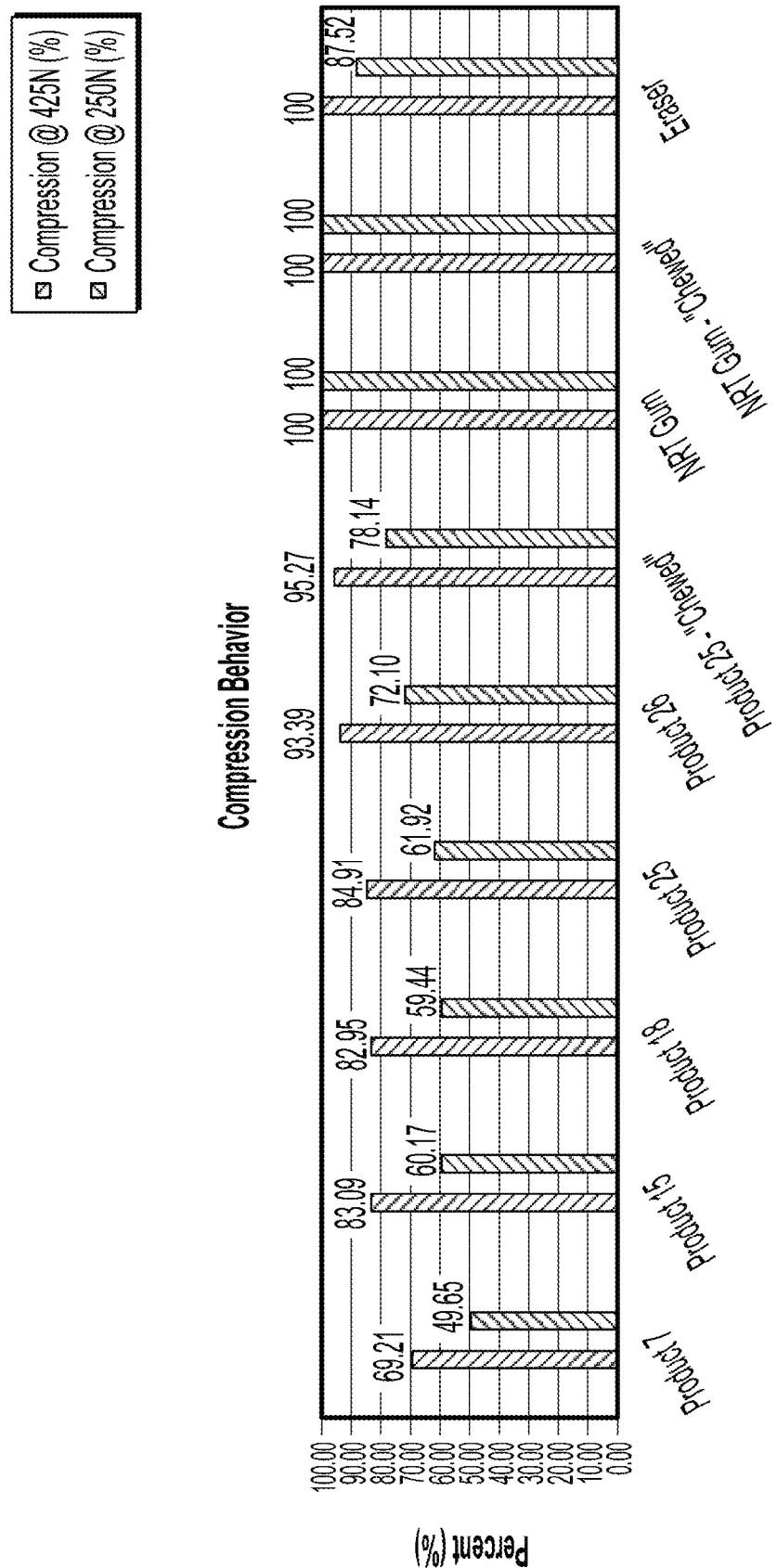
FIGS. 9A and 9B depict compression and springiness test results.

In some embodiments, the oral product 110 has a percentage of compression @250 N of less than 95%. In certain embodiments, the oral product 110 has a percentage of compression @250 N of less than 90%, less than 85%, or less than 80%. In certain embodiments, the oral product 110 has a percentage of compression @250 N of at least 10%, at least 25%, or at least 40%. For example, the oral product can have a percentage of compression @250 N of between 45% and 80%. In some embodiments, the oral product 110 has a percentage of compression @425 N of less than 99%. In certain embodiments, the oral product 110 has a percentage of compression @425 N of less than 98%, less than 97%, or less than 96%. In certain embodiments, the oral product 110 has a percentage of compression @425 N of at least 10%, at least 25%, at least 50%, or at least 60%. For example, the oral product can have a percentage of compression @425 N of between 65% and 98%. FIG. 9A, discussed in more detail below, depicts examples of compression test results for certain embodiments of oral products, for gum (both chewed and fresh), and for an eraser.

Figure 9B:
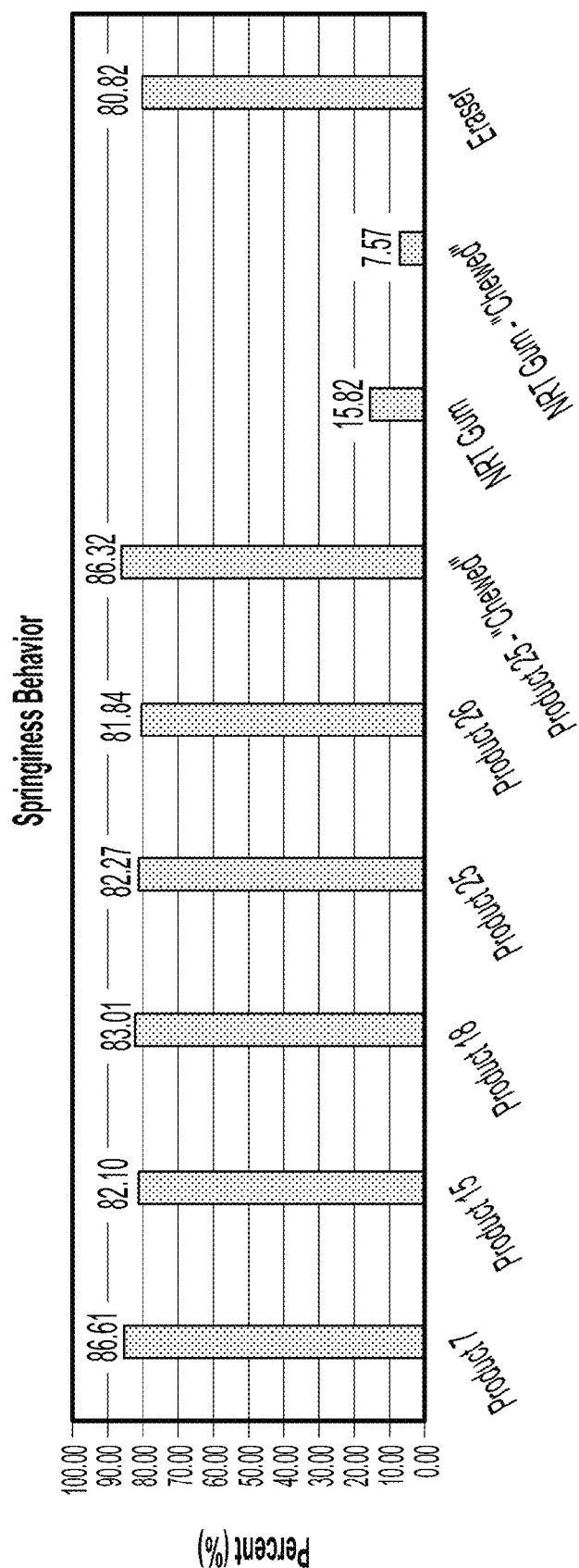

The springiness of a sample can be measured by measuring the percentage of recovery after a sample is compressed. As used herein, the term "percentage of springiness" means the percentage of thickness recovery of the sample during a 30 second recovery time after being compressed by the compression @425 N test using the 10 mm-diameter-sphere-tipped probe. For example, if a sample is compressed from an original thickness of 3.0 mm to a thickness of 2.0 mm and then recovers to 2.5 mm after 30 seconds, the springiness of the sample would be 50%. In some embodiments, the oral product 110 has a percentage of springiness of at least 20%. In certain embodiments, the oral product 110 has a percentage of springiness of at least 40%, at least 50%, at least 60%, at least 70%, at least 75%, or at least 80%. In certain embodiments, the percentage of springiness is less than 95%, less than 90%, or less than 87%. For example, the oral product can have a percentage of springiness of between 75% and 90%. FIG. 9B, discussed in more detail below, depicts examples of springiness test results for certain embodiments of oral products, for gum (both chewed and fresh), and for an eraser.

The particular materials used in the oral product 110 and the processing techniques discussed below can have an impact on the compressibility and springiness of the oral product. In addition to different materials have different compressibility and springiness properties, the incorporation of air bubbles or channels, or different fillers and/or fibers can also have an impact on the elasticity and pliability of the oral product. Additionally, the material properties of the overall oral product 110 can change as additives are released. In some embodiments, fibers and/or fillers can also dissolve or disintegrate during use and thus alter the material properties of the oral product 110 during use.

The oral product 110 can have a variety of colors. In some embodiments, the oral product 110 has an off-white color. In other embodiments, natural and artificial coloring can be added to the mouth-stable polymer before or during the molding process to form oral products 110 having a predetermined color. Encapsulated flavors can be added during the extrusion process to create speckles, patterns or dots within the oral product.

Polymers

The mouth-stable polymer can be a variety of different biocompatible and biostable polymers. In some embodiments, the mouth-stable polymer is a polymer generally recognized as safe by an appropriate regulatory agency. In some embodiments, the polymer is a thermoplastic polymer. The polymer can also be a thermoplastic elastomer. For example, suitable mouth-stable polymers include polyurethanes, silicon polymers, polyesters, polyacrylates, polyethylenes, polypropylenes, polyetheramides, polystyrenes (e.g., acrylonitrile butadiene styrene, high impact polystyrenes (HIPS)) polyvinyl alcohols, polyvinyl acetates, polyvinyl chlorides, polybutyl acetates, butyl rubbers (e.g., polyisobutylenes), SEBS, SBS, SIS, and mixtures and copolymers thereof. In certain embodiments, the mouth-stable polymer is food-grade or medical-grade polymers (e.g., medical-grade polyurethane).

The mouth-stable polymer forms the mouth-stable polymer matrix of the oral product 110. In some embodiments, the oral product includes at least 10 weight percent of one or more mouth-stable polymers. In certain embodiments, the oral product includes at least 20 weight percent, at least 30 weight percent, at least 40 weight percent, at least 50 weight percent, at least 60 weight percent, at least 70 weight percent, at least 80 weight percent, or at least 90 weight percent of one or more mouth-stable polymers. In certain embodiments, the oral product includes between 10 and 90 weight percent of one or more mouth-stable polymers. Accordingly to some embodiments, the oral product includes between 40 and 80 weight percent of the mouth-stable polymers. Some embodiments of the oral product have between 55 and 70 weight percent polymers.

The mouth-stable polymer according to certain embodiments has a flexural modulus of at least 5 MPa when tested according to ASTM Testing Method D790 or ISO 178 at 23 degrees Celsius. In some embodiments, the flexural modulus is at least 10 MPa. For example, the flexural modulus can be between 10 MPa and 30 MPa. In some embodiments, the mouth-stable polymer is a grade that complies with food-contact regulations applicable in one or more countries (e.g., US FDA regulations). In some embodiments, the mouth-stable polymer can be a polyurethane, SIS, or other thermal plastic elastomer meeting the requirements of the FDA-modified ISO 10993, Part 1 "Biological Evaluation of Medical Devices" tests with human tissue contact time of 30 days or less. The mouth-stable polymer can have a shore Hardness of 50D or softer, a melt flow index of 3 g/10 min at 200° C./10 kg, a tensile strength of 10 MPa or more (using ISO 37), and a ultimate elongation of less than 100% (using ISO 37).

Additives

A variety of additives can be included in the oral product 110. The additives can include alkaloids (e.g., nicotine), minerals, vitamins, dietary supplements, nutraceuticals, energizing agents, soothing agents, coloring agents, amino acids, chemsthetic agent, antioxidants, food grade emulsifiers, pH modifiers, botanicals (e.g., green tea), teeth whitening (e.g., SHRIMP), therapeutic agents, sweeteners, flavorants, and combinations thereof. In certain embodiments, the additives include nicotine, sweeteners, and flavorants. With certain combinations of nicotine, sweeteners, and flavorants, the oral product may provide a flavor profile and tactile experience similar to certain tobacco products.

Nicotine

Nicotine within the oral product can be tobacco-derived nicotine, synthetic nicotine, or a combination thereof. In certain embodiments, the oral product includes between 0.1 mg and 6.0 mg of nicotine. In some of these embodiments, the oral product includes between 1.0 mg and 3.0 mg of nicotine.

Tobacco-derived nicotine can include one or more other tobacco organoleptic components other than nicotine. The tobacco-derived nicotine can be extracted from raw (e.g., green leaf) tobacco and/or processed tobacco. Processed tobaccos can include fermented and unfermented tobaccos, dark air-cured, dark fire cured, burley, flue cured, and cigar filler or wrapper, as well as the products from the whole leaf stemming operation. The tobacco can also be conditioned by heating, sweating and/or pasteurizing steps as described in U.S. Publication Nos. 2004/0118422 or 2005/0178398. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. By processing the tobacco prior to extracting nicotine and other organoleptic components, the tobacco-derived nicotine may include ingredients that provide a favorable experience.

The tobacco-derived nicotine can be obtained by mixing cured and fermented tobacco with water or another solvent (e.g., ethanol) followed by removing the insoluble tobacco material. The tobacco extract may be further concentrated or purified. In some embodiments, select tobacco constituents can be removed. Nicotine can also be extracted from tobacco in the methods described in the following patents: U.S. Pat. Nos. 2,162,738; 3,139,436; 3,396,735; 4,153,063; 4,448,208; and 5,487,792.

The nicotine can also be purchased from commercial sources, whether tobacco-derived or synthetic. In other embodiments, the oral product can include a derivative of nicotine (e.g., a salt of nicotine).

Antioxidants

The oral product 110 can also include one or more antioxidants. In some embodiments, an oral product 110 can include a combination of nicotine and antioxidants. Antioxidants can result in a significant reduction in the conversion of nicotine into nicotine-N-oxide when compared to oral products without antioxidants. In some cases, an oral product can include 0.01 and 5.00 weight percent antioxidant, between 0.05 and 1.0 weight percent antioxidant, between 0.10 and 0.75 weigh percent antioxidant, or between 0.15 and 0.5 weight percent antioxidant. Suitable examples of antioxidants include ascorbyl palmitate (a vitamin C ester), BHT, ascorbic acid (Vitamin C), and sodium ascorbate (Vitamin C salt). In some embodiments, monosterol citrate, tocopherols, propyl gallate, tertiary butylhydroquinone (TBHQ), butylated hydroxyanisole (BHA), Vitamin E, or a derivative thereof can be used as the antioxidant. For example, ascorbyl palmitate can be the antioxidant in the formulations listed in Table I. Antioxidants can be incorporated into the polymer (e.g., polyurethane) during an extrusion process or after the polymer is extruded (e.g., during a post-extrusion flavoring process).

Table I (below) compares a test sample with a control sample to compare how the inclusion of antioxidant in an oral product 110 impacts the about of nicotine-N-oxide formed in the oral product after aging for 2 weeks and 4 weeks. The ambient samples were held at 25° C. and 65% relative humidity. Both the control and test samples included 1.5 mg of nicotine per piece. As shown, the inclusion of antioxidant significantly reduces the amount of nicotine-N-oxide formed in the oral product 110.

TABLE I

|  | Nicotine N Oxide | | % Difference between |
| --- | --- | --- | --- |
|  | Control* | Test** | Test and Control |
| Week 0 | 0.023% | 0.035% | — |
| Ambient Week 2 | 0.510% | 0.156% | −69.49% |
| Ambient Week 4 | 0.735% | 0.261% | −64.51% |
| Ambient Week 6 | 0.893% | 0.277% | −69.04% |
| Ambient Week 8 | 0.950% | 0.449% | −52.68% |
| Ambient Week 10 | 0.890% | 0.491% | −44.87% |
| Ambient Week 12 | 1.009% | 0.539% | −46.64% |

*The control is free of antioxidant, but includes 1.5 mg nicotine.
**The test includes about 0.15% ascorbyl palmitate antioxidant and about 1.5 mg nicotine.

In some cases, the oral product 110 can have a conversion of less than 0.50% of nicotine into nicotine-N-oxide after aging the oral product 110 for 2 weeks at 25° C. and 65% relative humidity. In some cases, the oral product 110 can have a conversion of less than 0.20% of nicotine into nicotine-N-oxide after aging the oral product 110 for 2 weeks at 25° C. and 65% relative humidity. In some cases, the oral product 110 can have a conversion of less than 0.70% of nicotine into nicotine-N-oxide after aging the oral product 110 for 4 weeks at 25° C. and 65% relative humidity. In some cases, the oral product 110 can have a conversion of less than 0.30% of nicotine into nicotine-N-oxide after aging the oral product 110 for 4 weeks at 25° C. and 65% relative humidity. In some cases, the oral product 110 can have a conversion of less than 0.80% of nicotine into nicotine-N-oxide after aging the oral product 110 for 6 weeks at 25° C. and 65% relative humidity. In some cases, the oral product 110 can have a conversion of less than 0.40% of nicotine into nicotine-N-oxide after aging the oral product 110 for 6 weeks at 25° C. and 65% relative humidity. In some cases, the oral product 110 can have a conversion of less than 0.30% of nicotine into nicotine-N-oxide after aging the oral product 110 for 6 weeks at 25° C. and 65% relative humidity. In some cases, the oral product 110 can have a conversion of less than 0.85% of nicotine into nicotine-N-oxide after aging the oral product 110 for 8 weeks at 25° C. and 65% relative humidity. In some cases, the oral product 110 can have a conversion of less than 0.50% of nicotine into nicotine-N-oxide after aging the oral product 110 for 8 weeks at 25° C. and 65% relative humidity. In some cases, the oral product 110 can have a conversion of less than 0.85% of nicotine into nicotine-N-oxide after aging the oral product 110 for 10 weeks at 25° C. and 65% relative humidity. In some cases, the oral product 110 can have a conversion of less than 0.55% of nicotine into nicotine-N-oxide after aging the oral product 110 for 10 weeks at 25° C. and 65% relative humidity. In some cases, the oral product 110 can have a conversion of less than 0.95% of nicotine into nicotine-N-oxide after aging the oral product 110 for 12 weeks at 25° C. and 65% relative humidity. In some cases, the oral product 110 can have a conversion of less than 0.60% of nicotine into nicotine-N-oxide after aging the oral product 110 for 12 weeks at 25° C. and 65% relative humidity.

The presence of antioxidant can also reduce the formation of other tobacco derived impurities, such as Cotinine and myosime, as shown in Table II (below). Antioxidant level 1 is 0.075% in the formula and level 2 is 0.15% in the formula. The control sample includes no antioxidant. The antioxidant is ascorbyl palmitate.

TABLE II

| | | Week 4 | | | | | | | |
| --- | --- | --- | --- | --- | --- | --- | --- | --- | --- |
| Storage | | % Relative to Nicotine Concentration (Average, n = 3) | | | | | | | |
| Conditions | Packaging Type | Myosmine | Nornicotine | Anabasine | Cotinine | Anatabine | Nicotine-Oxide | b-Nicotyrine | Total |
| Ambient | Control | 0.125% | 0.014% | ND | 0.023% | ND | 0.735% | 0.017% | 0.913% |
| (25° C., 60 RH) | AO Level 1 | 0.041% | 0.018% | ND | 0.007% | ND | 0.188% | 0.009% | 0.263% |
| | AO Level 2 | 0.038% | 0.029% | ND | 0.007% | ND | 0.261% | 0.008% | 0.343% |

Sweeteners

A variety of synthetic and/or natural sweeteners can be used as additives in the oral product 110. Suitable natural sweeteners include sugars, for example, monosaccharides, disaccharides, and/or polysaccharide sugars, and/or mixtures of two or more sugars. According to some embodiments, the oral product 110 includes one or more of the following: sucrose or table sugar; honey or a mixture of low molecular weight sugars not including sucrose; glucose or grape sugar or corn sugar or dextrose; molasses; corn sweetener; corn syrup or glucose syrup; fructose or fruit sugar; lactose or milk sugar; maltose or malt sugar or maltobiose; sorghum syrup; mannitol or manna sugar; sorbitol or d-sorbite or d-sobitol; fruit juice concentrate; and/or mixtures or blends of one or more of these ingredients. The oral product 110 can also include non-nutritive sweeteners. Suitable non-nutritive sweeteners include: stevia, saccharin; Aspartame; sucralose; or acesulfame potassium.

Flavorants

The oral product 110 can optionally include one or more flavorants. The flavorants can be natural or artificial. For example, suitable flavorants include wintergreen, cherry and berry type flavorants, various liqueurs and liquors (such as Dramboui, bourbon, scotch, and whiskey) spearmint, peppermint, lavender, cinnamon, cardamon, *apium* graveolents, clove, cascarilla, nutmeg, sandalwood, bergamot, geranium, honey essence, rose oil, vanilla, lemon oil, orange oil, Japanese mint, *cassia*, caraway, cognac, jasmin, chamomile, menthol, ylang ylang, sage, fennel, pimenta, ginger, anise, coriander, coffee, liquorish, and mint oils from a species of the genus *Mentha*, and encapsulated flavors. Mint oils useful in particular embodiments of the oral product 110 include spearmint and peppermint. Synthetic flavorants can also be used. In certain embodiments, a combination of flavorants can be combined to imitate a tobacco flavor. The particular combination of flavorants can be selected from the flavorants that are generally recognized as safe ("GRAS") in a particular country, such as the United States. Flavorants can also be included in the oral product as encapsulated flavorants.

In some embodiments, the flavorants in the oral product 110 are limited to less than 20 weight percent in sum. In some embodiments, the flavorants in the oral product 110 are limited to be less than 10 weight percent in sum. For example, certain flavorants can be included in the oral product 110 in amounts of about 1 weight percent to 5 weight percent.

Other Additives

The oral product 110 may optionally include other additives. For example, these additives can include non-nicotine alkaloids, dietary minerals, vitamins, dietary supplements, therapeutic agents, and fillers.

Oral products 110 can also include vitamins, dietary minerals, other dietary supplements, and/or therapeutic agents. For example, suitable vitamins include vitamins A, B1, B2, B6, C, D2, D3, E, F, K, and P. For example, an oral product 110 can include C-vitamins with nicotine. Suitable dietary minerals include calcium (as carbonate, citrate, etc.) or magnesium (as oxide, etc.), chromium (usually as picolinate), and iron (as bis-glycinate). One or more dietary minerals could be included in an oral product with or without the use of other additives. Other dietary supplements and/or therapeutic agents can also be included as additives.

The oral product 110 can also include fillers such as starch, di-calcium phosphate, lactose, sorbitol, mannitol, and microcrystalline cellulose, calcium carbonate, dicalcium phosphate, calcium sulfate, clays, silica, glass particles, sodium lauryl sulfate (SLS), glyceryl palmitostearate, sodium benzoate, sodium stearyl fumarate, talc, and stearates (e.g., Mg or K), and waxes (e.g., glycerol monostearate, propylene glycol monostearate, and acetylated monoglycerides), stabilizers (e.g., ascorbic acid and monosterol citrate, BHT, or BHA), disintegrating agents (e.g., starch, sodium starch glycolate, cross caramellose, cross linked PVP), pH stabilizers, or preservatives. In some embodiments, the amount of filler in the oral product 110 is limited to less than 10 weight percent in sum. In some embodiments, the amount of filler in the oral product 110 is limited to be less than 5 weight percent in sum. In some embodiments, the fillers are mouth stable. In other embodiments, the fillers can dissolve or disintegrate during use and thus result in an oral product that becomes more pliable during use.

Fibers

The oral product can include fibers within the mouth-stable polymer matrix. As will be discussed below, the fibers can be mixed with the mouth-stable polymer prior to or during an extrusion process. As shown in FIG. 4, the fibers provide passages in the mouth-stable polymer matrix, which can permit certain additives within the mouth-stable polymer matrix to be released into an oral cavity when the oral product is received in an oral cavity and exposed to saliva. The additives can be absorbed in fiber-polymer matrix and/or form pockets within the mouth-stable polymer matrix, which can be accessed via the fibers 130.

Figure 4A:
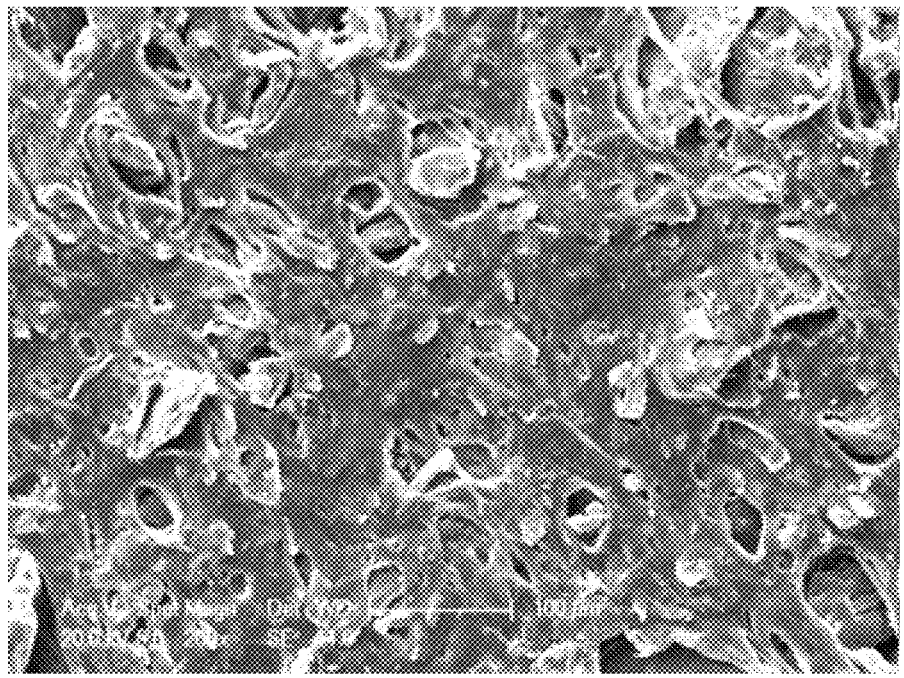
FIGS. 4A-4C are magnified pictures of cross-sections of an oral product.
Figure 4B:
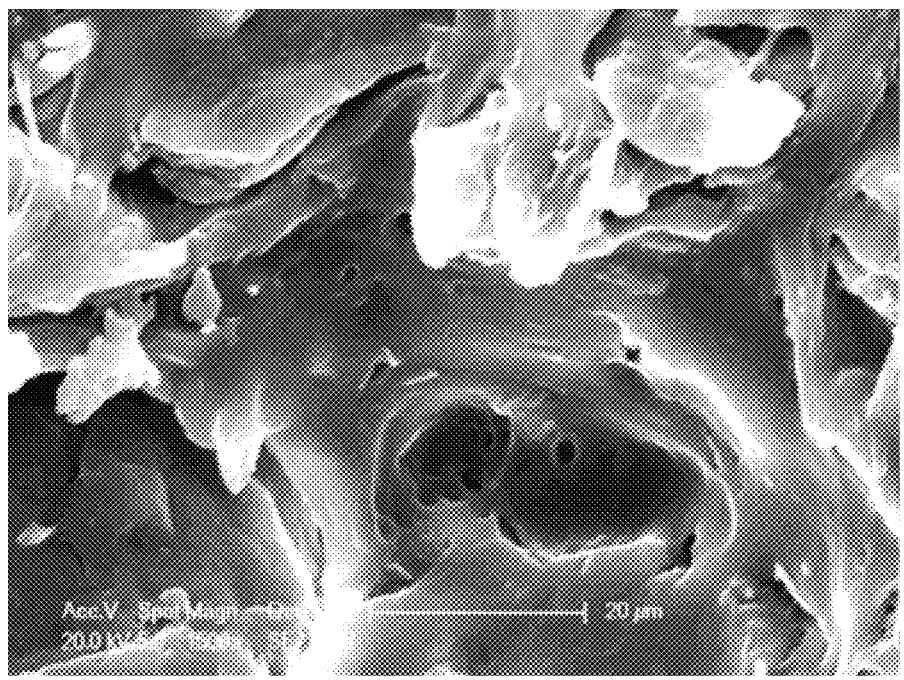
Figure 4C:
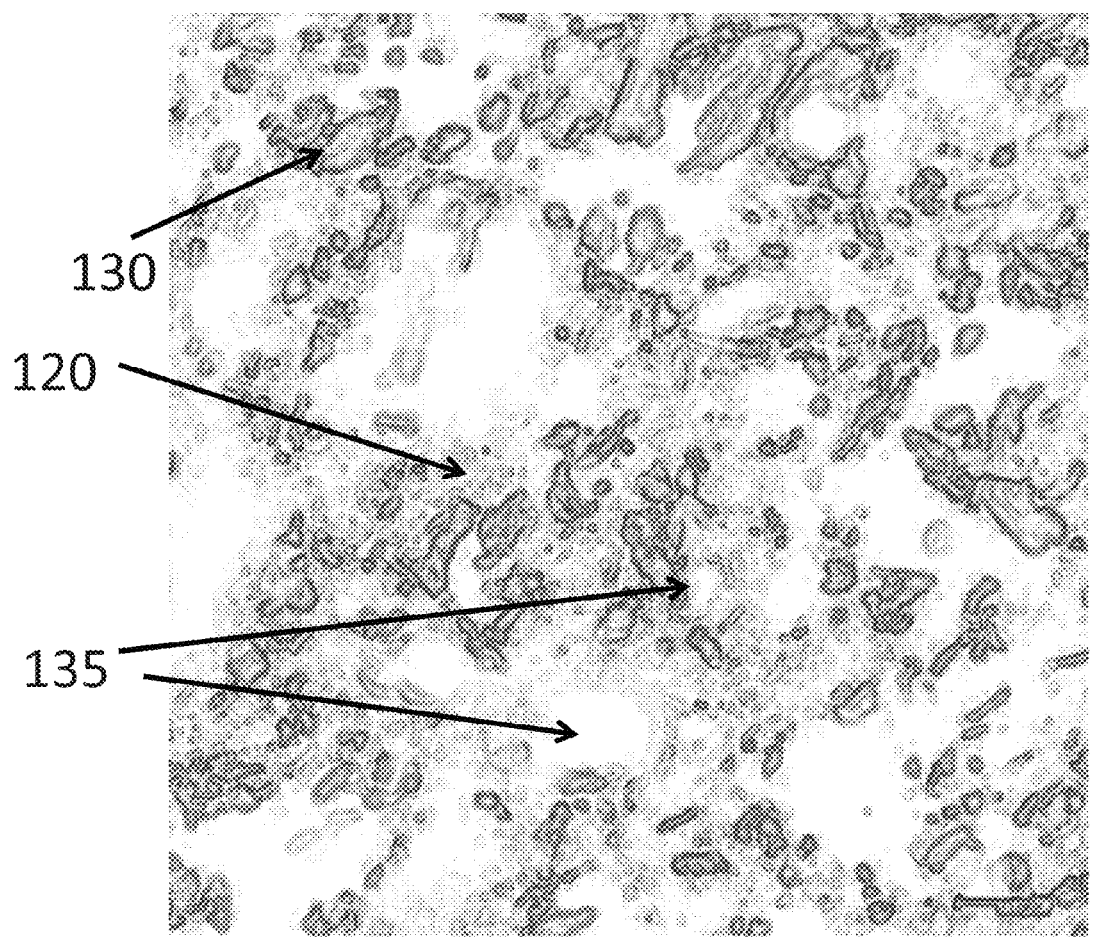

FIGS. 4A-4C depicts cross-sections of oral products 100. FIGS. 4A and 4B are images from a scanning electron microscope (SEM) (XL30 ESEM TMP, FEI/Philips, the Netherlands). The SEM microscope was operated at 20 kV electron acceleration voltage and images were recorded at different magnifications. FIG. 4A is an SEM image showing the porous structure of the mouth stable polymer matrix 120.

FIG. 4A highlights pores 135a having diameters of between 20 and 60 microns. FIG. 4B is also an SEM image showing the porous structure of the mouth stable polymer matrix 120. FIG. 2B, however, has an increased magnification, thus pores 135b having diameters of between 1 and 10 microns can be seen.

FIG. 4C is a confocal laser scanning microscopy (CLSM) image. In CLSM, only fluorescent labeled materials are visible. The product was stained with the fluorescent dyes of acridinorange and acriflavine, respectively. The light source was an Argon laser using $\lambda$ex=488 nm (acridinorange) and a HeNE laser using $\lambda$ex=594 nm (acriflavin). The signals were emitted in the wavelength interval of 500-550 nm and 610-650 nm. FIG. 4C was converted into gray scale for the purposes of this application. The darker areas show the placement of fibers 130 in the mouth-stable polymer matrix. The lighter grey areas show the mouth-stable polymer 120 (in this case, polyurethane). The white areas in the image are pores in the structure. In some embodiments, the fibers are hydrophilic such that water-soluble additives can be wicked by the fibers. In some embodiments, the fibers can dissolve to leave channels. Additives can be present in the pores 135 of the mouth-stable polymer matrix 120.

The fibers can be cellulosic fibers. The cellulosic fibers can be derived from plant tissue. In some embodiments, the cellulosic fibers include cellulose. The cellulosic fibers can further include lignin and/or lipids. Suitable sources for cellulosic fibers include wood pulp, cotton, sugar beets, bran, citrus pulp fiber, switch grass and other grasses, Salix (willow), tea, and Populus (poplar). In some embodiments, the cellulosic fibers can be chopped or shredded plant tissue comprising various natural flavors, sweeteners, or active ingredients. In some embodiments, the oral product 110 can include nicotine as an additive (optionally with additional sweeteners and flavors) and non-tobacco cellulosic fiber, and thus be substantially free of tobacco plant tissue.

The cellulosic fibers can have a variety of dimensions. The dimensions of the fibers (in addition to the amount) can impact the release characteristics of the additives. For example, cellulosic fibers can be hydrophilic, thus water soluble additives (e.g., nicotine) can preferentially be absorbed in fiber-polymer matrix. As will be discussed in the Examples below, the release profile of nicotine from a polyurethane oral product 110 can be impacted by both the fiber sizes and the amounts of fiber. In certain embodiments, the cellulosic fiber can be processed to have an average fiber size of less than 200 micrometers. In particular embodiments, the fibers are between 75 and 125 micrometers. In other embodiments, the fibers are processed to have a size of 75 micrometers or less.

The oral product 110 can also include soluble fibers. The soluble fibers can be adapted to dissolve when exposed to saliva when the oral product 110 is received in an oral cavity. In some embodiments, the soluble fiber can be a maltodextrin. The maltodextrin can be derived from corn. For example, Soluble Dietary Fiber can be included in an oral product 110. Soluble fibers can be used alone or with cellulosic fibers to provide channels 135 for additives 140 and/or 142 to be released from the oral product 110. As the soluble fibers dissolve, the oral product 110 can become more flexible and the additional channels can open up to permit the release of additional additive deposits 140 or 142. Suitable soluble fibers include psyllium fibers. In other embodiments, the fibers can be partially soluble. For example, sugar beet fibers can partially dissolve during use.

In some embodiments, an oral product 110 can include a combination of soluble and insoluble fibers. The ratio of soluble to insoluble fiber can impact the softness of texture of the oral product 110. The ratio of soluble to insoluble fiber can also impact the compressibility of the oral product 110. In some embodiments, a ratio of soluble to insoluble fiber is between 1:60 and 60:1. In some embodiments, the ratio of soluble to insoluble fiber is greater than 1:50, greater than 1:40, greater than 1:30, greater than 1:20, greater than 1:10, or greater than 1:5. In some embodiments, the ratio of soluble to insoluble fiber is less than 1:1, less than 1:2, less than 1:5, less than 1:10, less than 1:20, or less that 1:30. In some case, an oral product having a mixture of soluble and insoluble fibers can have a percentage of compression @250 N of between 60 percent and 98 percent, between 65 percent and 95 percent, between 70 percent and 90 percent, or between 80 and 89 percent.

Table III, below, depicts the percentage of compression @250 N for oral products having different percentages of soluble and insoluble fibers. As shown, the inclusion of soluble fiber can increase the compressibility of the oral product, which can also be perceived as a softer mouth feel by an adult tobacco consumer. The soluble and the insoluble fiber depicted in Table I were pre-mixed and added into the process via a single feeder, but separate fiber feeders can also be added. For example, larger commercial processes can include additional fiber feeders to meter the insoluble and soluble fiber separately to produce a desired ratio.

TABLE III

| Prototype # | Compression @250N | Soluble Fiber FiberSol-2 ™ | Insoluble Fiber | Polyurethane | Antioxidant |
| --- | --- | --- | --- | --- | --- |
| Control | 60% | 0.0% | 31.392% | 56.505% | 0.0% |
| Sample A | 72% | 1.162% | 30.981% | 55.765% | 0.148% |
| Sample B | 83% | 2.351% | 28.994% | 56.421% | 0.15% |
| Sample C | 88% | 2.344% | 28.907% | 56.252% | 0.448% |

Plasticizers

The oral product 110 can also include one or more plasticizers. Plasticizers can soften the final oral product and thus increase its flexibility. Plasticizers work by embedding themselves between the chains of polymers, spacing them apart (increasing the "free volume"), and thus significantly lowering the glass transition temperature for the plastic and making it softer. Suitable plasticizers include propylene glycol, glycerin, vegetable oil, and medium chain triglycerides. In some embodiments, the plasticizer can include phthalates. Esters of polycarboxylic acids with linear or branched aliphatic alcohols of moderate chain length can also be used as plasticizers. Moreover, plasticizers can facilitate the extrusion processes described below. In some embodiments, the oral product 110 can include up to 20 weight percent plasticizer. In some embodiments, the oral product 110 includes between 0.5 and 10 weight percent plasticizer, the oral product 110 can include between 1 and 8 weight percent plasticizer, or between 2 and 4 weight percent plasticizer. For example, an oral product comprising a polyurethane polymer matrix and include about 3 to 6.5 weight percent of propylene glycol.

Molding Processes

Figure 5A:
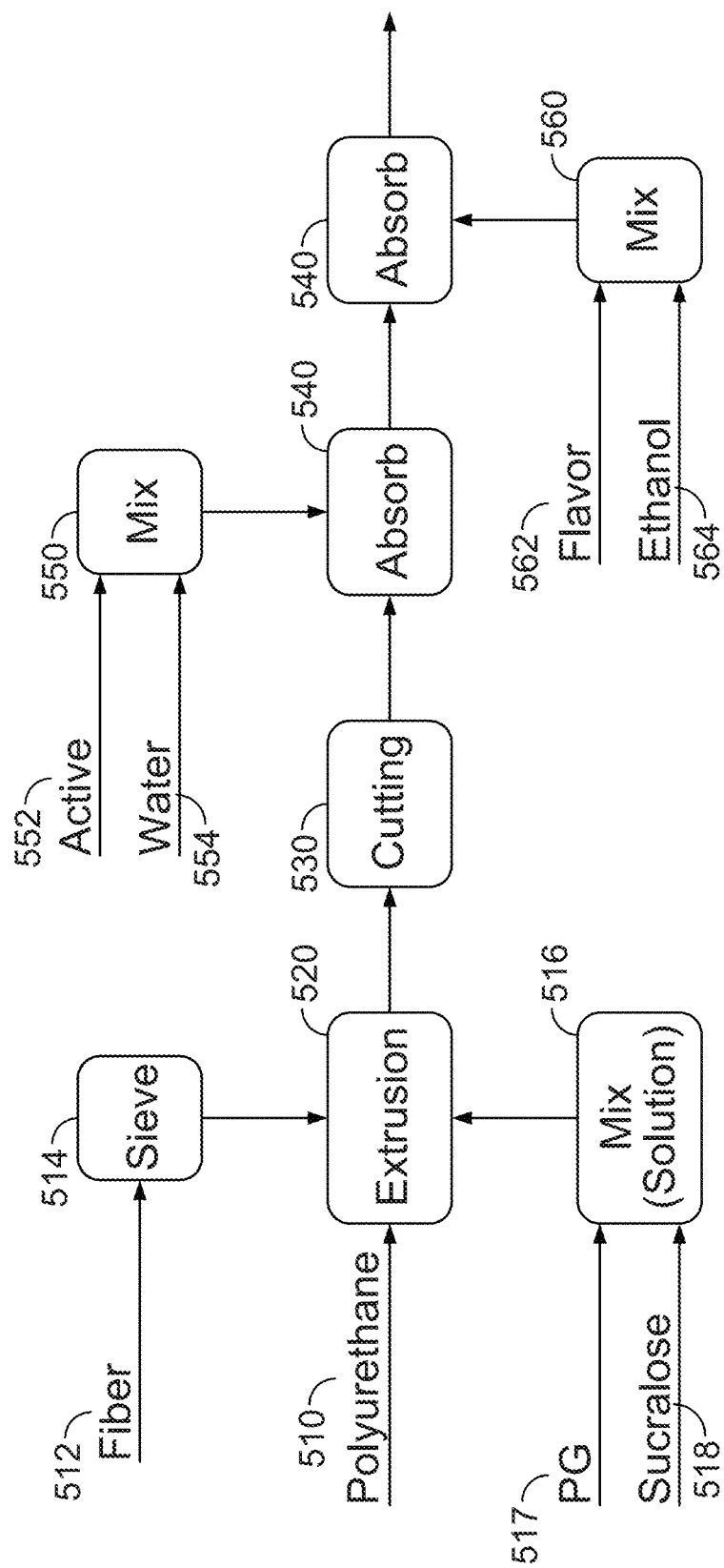
FIG. 5A illustrates a process diagram for making oral products according to some embodiments.
Figure 5B:
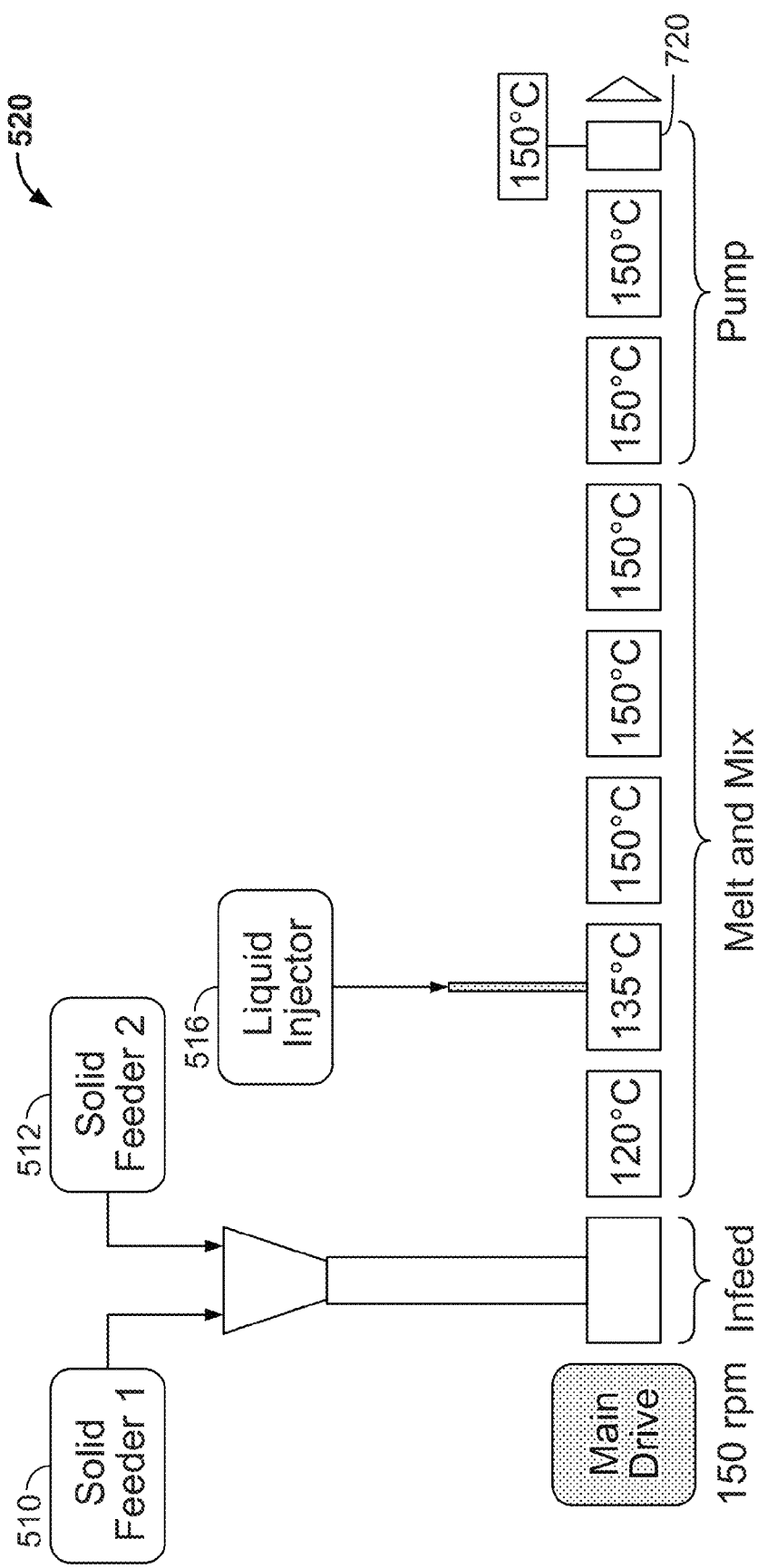
FIG. 5B illustrates an extruder configuration for making oral products according to some embodiments.

The oral product 110 can be produced by extruding a mouth-stable polymer (e.g., polyurethane) with fibers (e.g., cellulosic fiber) and/or additive (e.g., nicotine) to form a rod of a mouth-stable polymer matrix including fibers and/or additives. The rod is cut into individual oral products 110. FIGS. 5A and 5B depict exemplary methods to form oral products 110.

Referring to the extrusion process illustrated in FIG. 5A, a mouth-stable polymer 510 (e.g., polyurethane) is introduced into an extruder for extrusion 520 along with fibers 512 (e.g., cellulosic fibers). The fibers 512 can be passed through a sieve 514 prior to introduction into the extruder. A mixture of additives 516 can also be introduced into the extruder. The mixture of additives 516 can be a solution (as shown). As shown, the additives can include a plasticizer 517 (e.g., propylene glycol) and a sweetener 518 (e.g., sucralose). The mixture of additives can also be provided in slurry form or a dry mix of powdered additives.

Figure 7:
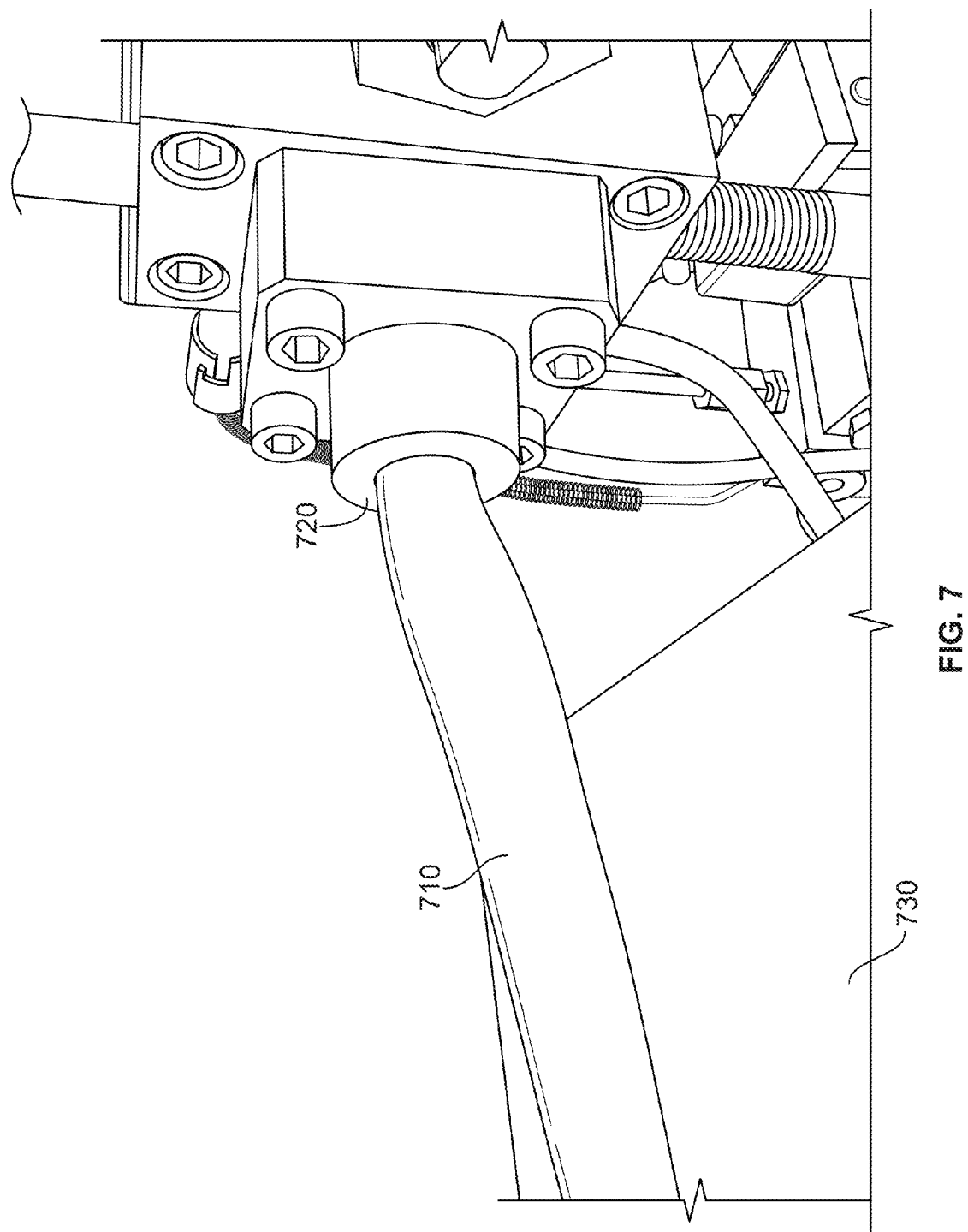
FIG. 7 illustrates a rod of mouth-stable polymer exiting an extruder die.

FIG. 5B illustrates an example of how the mouth-stable polymer 510 (e.g., polyurethane) can be compounded with fiber 512 and a mixture of additives 516. As shown, polyurethane pellets 510 and cellulosic fibers 512 can be introduced into an infeed section of an extruder. A first section of the extruder melts and mixes the polymer, elevating the temperature to about 150° C. The mixture 516 of propylene glycol 517 and sucralose 518 can be injected into the extruder downstream of the infeed section of the extruder. The polymer/fiber/plasticizer/sweetener mixture can then be extruded out of an extrusion die 720 at a temperature of about 150° C. An example of an extrusion die is shown in FIG. 7. For example, the extruder of FIG. 5B can operate at a mass flow rate of about 1.8 lbs/hour.

The polymer-fiber combination can exit an extrusion die 720 as a rod 710 and onto a moving conveyor 730, as shown in FIG. 7. The size of the extrusion die 720, the take away speed of the moving conveyor 730, the mixture of polymer-fiber combination, and the temperature of the mixture exiting the die 720 can all have an impact on the final diameter of the rod 710.

Figure 8:
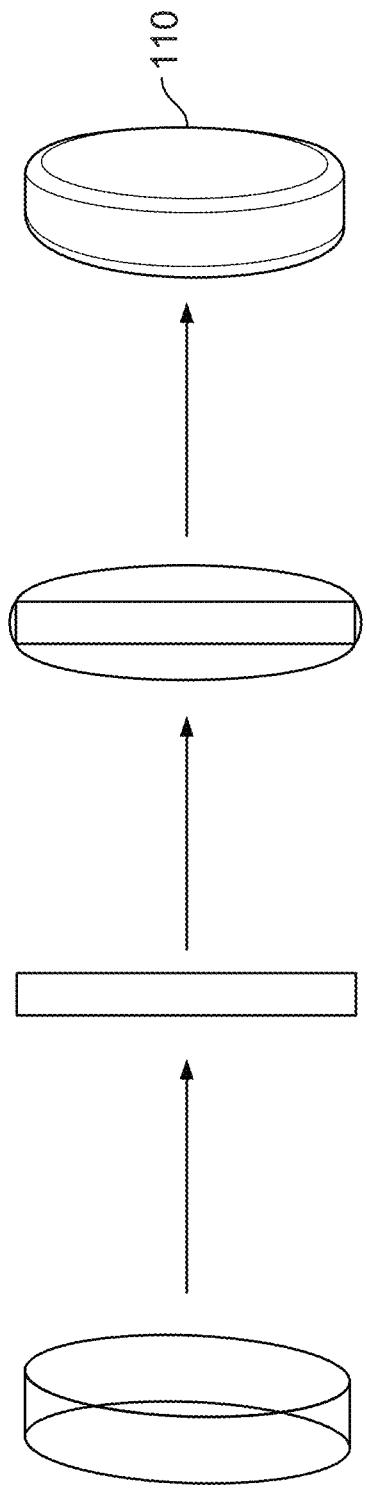
FIG. 8 illustrates how a cut piece of mouth-stable polymer including fibers and/or additives can pillow.

The extruded polymer-fiber rod 710 is then cut in a cutting process 530, as shown in FIG. 5A. The cutting can be hot-face cutting. Hot-face cutting can occur immediately after the rod 720 exits the extrusion die 720. The cutting can induce pillowing of the polymer matrix, as shown in FIG. 8. The cutting process 530 can also include a process of rounding the edges of the cut polymer-fiber composite. For example, a pelletizer can be used to round the edges. The pelletizer can also help to cool the oral products 110. In other embodiments, the extruded polymer-fiber rod 710 is cooled prior to cutting.

Before or after cutting, additional additives and/or flavorants can be added to the extruded polymer-fiber rod and/or pieces. As shown in FIG. 5A, a mixture of additives 550 and a mixture of flavorants 560 can be absorbed into polymer-fiber pieces in one or more absorbing processes 540. The mixture of additives 550 can include 552 and water 554. A mixture of flavorants 560 can include a flavor 562 (e.g., wintergreen) and a carrier 564 (e.g., ethanol). The oral products 110 could then be dried, packaged, and sealed.

Figure 6A:
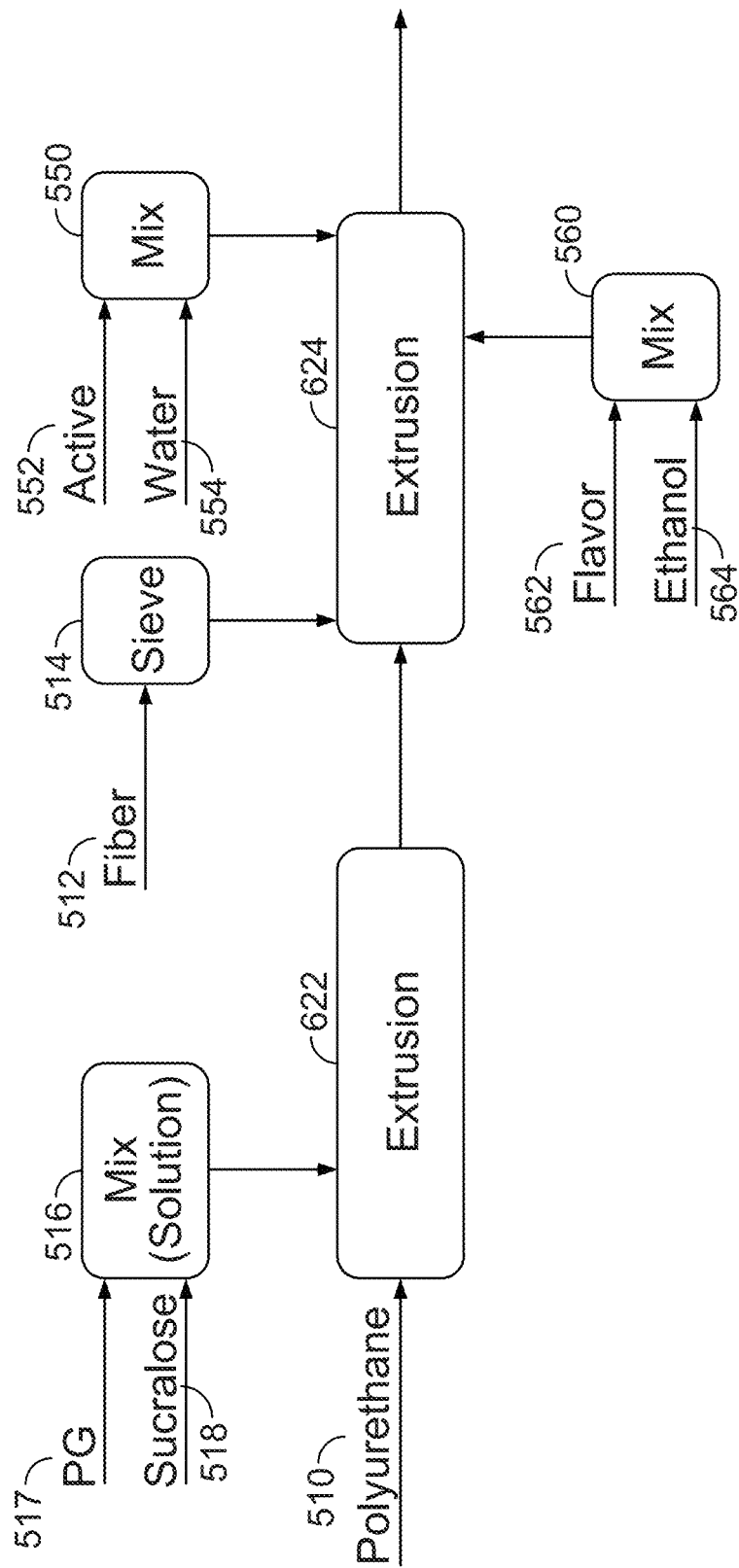
FIG. 6A illustrates a process diagram for making oral products according to other embodiments.

FIG. 6A depicts an alternative arrangement where a mouth-stable polymer 510 (e.g., polyurethane) is compounded with a mixture 516 of one or more plasticizers 517 (e.g., propylene glycol) and/or sweeteners 518 (e.g., sucralose) in a first extrusion process 622. The compounded polymer/plasticizer/sweetener mixture is then compounded with fiber 512 in a second extrusion process 624. As shown, additives such as nicotine 552 and/or flavorants 562 can also be added during the second extrusion process 624. In some embodiments, the compounding in the first extrusion process occurs at a higher temperature than the compounding during the second extrusion process. Both extrusion processes can occur in a single extruder.

Figure 6B:
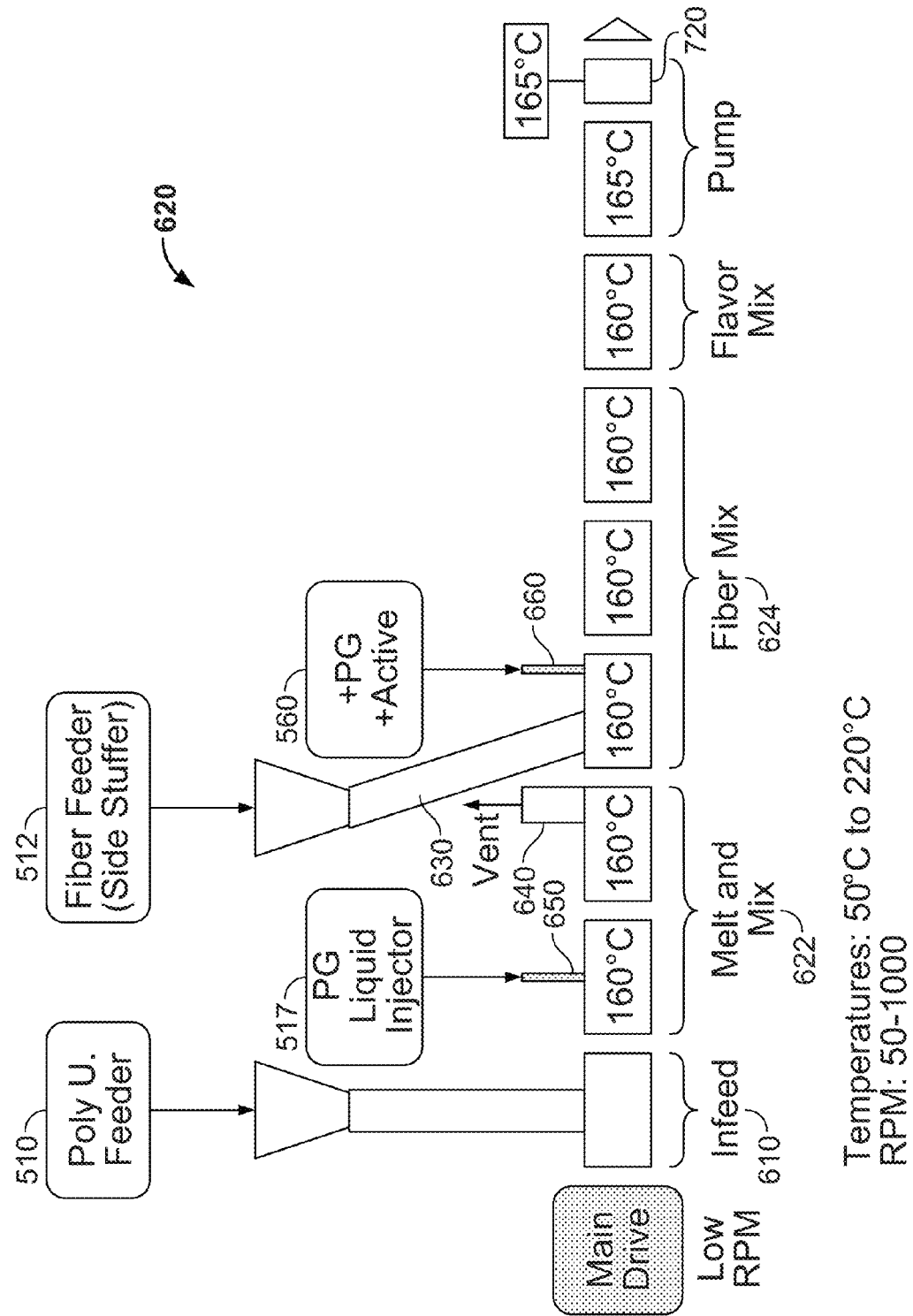
FIG. 6B illustrates an extruder configuration for making oral products according to certain embodiments

FIG. 6B depicts an arrangement of an extruder where the active, plasticizer, fibers and flavorants are all added the mouth-stable polymer in the extruder. Polyurethane pellets 510 are added to an infeed section 610 of the extruder 620. Plasticizer 517 (e.g., propylene glycol) (and optionally actives, sweeteners, and/or carriers) are injected into a first section of the extruder and compounded with the polyurethane. A vent 640 can be provided to release volatiles. Cellulosic fibers 512 can be introduced into the extruder through a side feeder 630. A flavorant mixture 560 can be added through liquid injector 660 in a flavor mixing section of the extruder. Active 52 (e.g., nicotine) and plasticizer 517 can also be injected through liquid injector 660. The mixture can then be extruded through an extrusion die 720 at a temperature of about 165° C. The extruded mixture can be hot-cut as it exits the extrusion die 720 and passed to a pelletizer. In other embodiments, the extruded mixture can be cooled on a cooling conveyer and cut. For example, the extruder of FIG. 6B can operate at a mass flow rate of about 5.5 lbs/hour. After cutting, the oral products 110 can be further flavored in a pan coater. The oral products 110 can then be sent to bulk storage and packaged.

In addition to the methods described above, there are many methods for making and shaping the oral products. In some embodiments, extruded and cut pieces can be introduced into a compression mold to form a final oral product shape. In other embodiments, the oral product 110 can be injection molded, compression molded, or injection-compression molded. Blocks of polymer, fiber, and/or additive can also be formed and machined into a desired shape.

EXAMPLES

Figure 9C:
FIG. 9C depicts some of the samples tested.
Figure 9C:
Figure 9C:
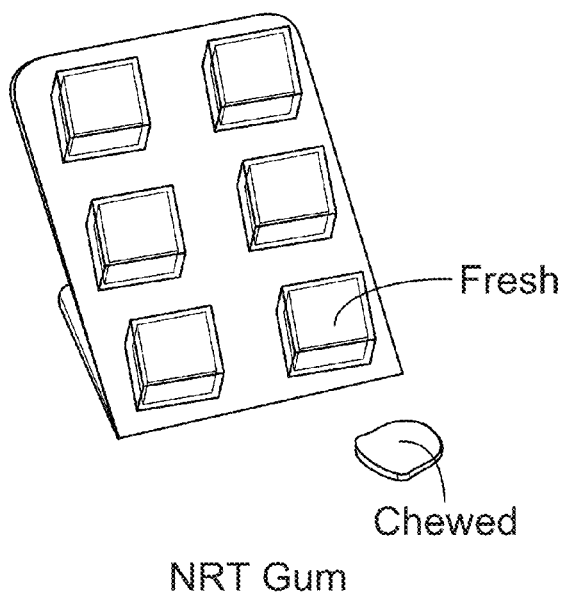
Figure 9C:
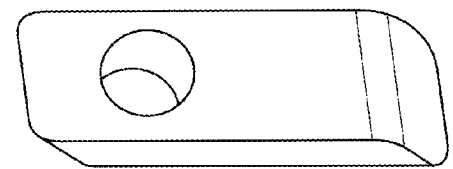
Figure 9C:
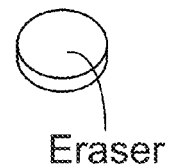

A series of oral products were produced by extruding a combination of polyurethane, cellulosic fiber, nicotine, propylene glycol, sweeteners, and flavorants to produce a variety of oral products, including the oral products listed in Table IV below. Each product sample was cut to have a thickness of about 3 mm. Each oral product (Products 7, 15, 18, 25, and 26) was subjected to the compression @250 N test, the compression @425 N test, and the springiness test discussed above. To compare the properties of the oral products 110, samples of nicotine replacement therapy (NRT) chewing gum[1] and a cut piece of a standard eraser[2] were also tested. The NRT gum was tested in both its natural state and after being chewed. A chewed sample of Product 25 was also tested. FIG. 9C depicts some of the samples. As shown in the chart and in FIGS. 9A and 9B, the oral products were less compressive than the chewing gum and the eraser. During the compression tests of the NRT gum, each sample was punctured by the probe, thus they are indicated as having a 100% compression. The eraser was also punctured by the compression @425 N test. The oral products, however, each withstood the compression tests. The non-zero values for the compression tests of the oral products, however, indicate that the oral products are pliable and can be worked within the mouth.

[1] Nicorette Original (2 mg).
[2] An eraser, also known as a rubber in the UK, is an article of stationery that is used for rubbing out pencil markings.

TABLE IV

| Analysis Date | Sample Number | Sample ID | Sample Thickness (mm) | Compression @ 250N (%) | Compression @ 425N (%) | Springiness (%) |
|---|---|---|---|---|---|---|
| Oct. 4, 2011 | 1 | Product 7 | 3.04 | 49.65 | 69.21 | 86.61 |
|  | 2 | Product 15 | 2.95 | 60.17 | 83.09 | 82.10 |
|  | 3 | Product 18 | 3.01 | 59.44 | 82.95 | 83.01 |
|  | 4 | Product 25 | 3.02 | 61.92 | 84.91 | 82.27 |
|  | 5 | Product 26 | 3.04 | 72.10 | 93.39 | 81.84 |
| Oct. 11, 2011 | 6 | Product 25-"chewed" | 2.88 | 78.14 | 95.27 | 86.32 |
|  | 7 | NRT Gum | 2.63 | 100* | 100* | 15.82 |
|  | 8 | NRT Gum-"chewed" | 2.72 | 100* | 100* | 7.57 |
|  | 9 | Eraser | 2.94 | 87.52 | 100* | 80.82 |

*Sample was fully compressed by the probe (resulting in a hole in the sample)

The oral products also demonstrated resilience in the springiness test discussed above. As shown, the NRT gum (both chewed and fresh) resulted in very little recovery after compression. The eraser, on the other hand, demonstrated a similar amount of springiness as compared to the oral products. These tests also demonstrate that the chewed oral product results in a more compressible product.

Figure 10A:
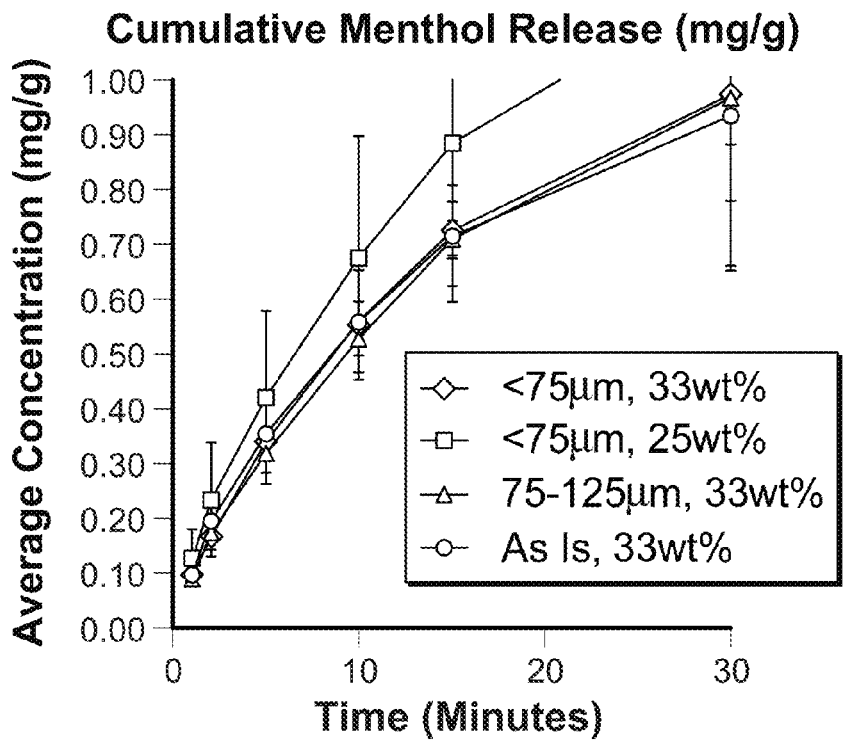
FIGS. 10A and 10B depict cumulative release timelines for menthol and nicotine from oral products.
Figure 10B:
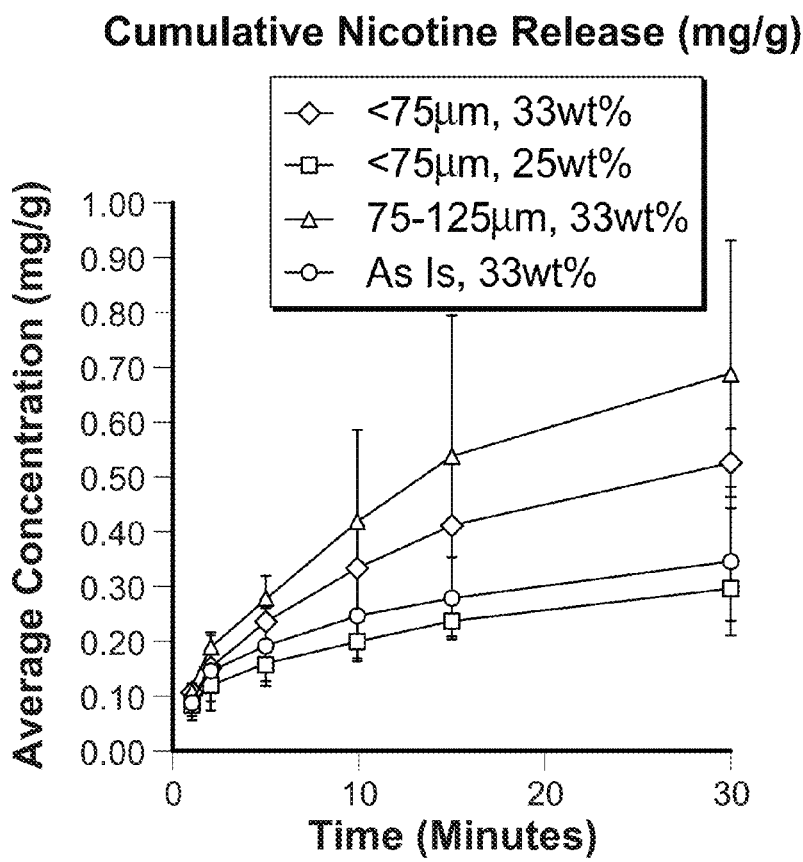

A series of oral products were also tested in a mastication test to determine the additive release profile. The results of this test are shown in FIGS. 10A and 10B. Each sample included polyurethane, cellulosic fiber, peppermint oil, and nicotine. The samples included about 2 mg of nicotine and about 1.6% total weight of peppermint oil. One constituent of peppermint oil is menthol. Peppermint oil may contain between 16 weight percent and 50 weight percent of menthol, usually about 30 weight percent, thus sampling the release of menthol is an appropriate way to approximate the release of peppermint oil. The different samples included different amounts of polymer (polyurethane), different amounts of cellulosic fiber, or different fiber sizes. Some of the samples had 59.70% polyurethane and 33.17% fiber, while other samples had 67.87% polyurethane and 25.00% fiber. Moreover, some of the samples had fiber having a size of less than 75 micrometers, some has a fiber size of between 75 and 125 micrometers, and some included bulk fiber. The samples also included nicotine and menthol (as a flavorant). Each sample was placed in a mastication tester that manipulated the sample in a solution that mimics saliva. At varying time intervals, samples were taken from the mastication tester to determine the total amount of menthol and nicotine released. As shown in FIGS. 10A and 10B, each sample continued to have a release of the additives even after 15 minutes of mastication. As compared to chewing gums, this is an increased additive release time period.

The release of menthol was accelerated in the sample having a higher percentage of polyurethane and a lower percentage of fiber. The release of the nicotine was accelerated by having a higher percentage of fiber and by having larger fiber sizes. Accordingly, the release rate of water-soluble additives may be determined by the amount of fibers and by the fiber dimensions in the oral product.

OTHER EMBODIMENTS

It is to be understood that, while the invention has been described herein in conjunction with a number of different aspects, the foregoing description of the various aspects is intended to illustrate and not limit the scope of the invention, which is defined by the scope of the appended claims. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. An oral product, comprising a body that is wholly receivable in an oral cavity, the body comprising:
    a mouth-stable polymer matrix comprising polyurethane, the oral product comprising at least 60 weight percent of one or more mouth-stable polymers;
    at least 10 weight percent of non-tobacco cellulosic fibers embedded in the mouth-stable polymer matrix, the cellulosic fibers comprising cellulose, the cellulosic fibers having an average fiber size of less than 200 micrometers; and
    nicotine or derivative thereof dispersed in the mouth-stable polymer matrix such that the nicotine or derivative thereof is released from the body when the body is received within the oral cavity and exposed to saliva, wherein the cellulosic fibers provide passages in the mouth-stable polymer matrix to pores retaining the nicotine or derivative thereof, the pores having diameters of between 20 and 60 microns, wherein the oral product is substantially free of tobacco plant tissue.

2. The oral product of claim 1, further comprising a plasticizer dispersed in the mouth-stable polymer matrix.

3. The oral product of claim 2, wherein the plasticizer is selected from the group consisting of propylene glycol, glycerin, vegetable oil, triglycerides, and combinations thereof.

4. The oral product of claim 1, further comprising a sweetener dispersed in the body.

5. The oral product of claim 4, wherein the sweetener is selected from the group consisting of saccharine, sucralose, aspartame, acesulfame potassium, and combinations thereof.

6. The oral product of claim 1, wherein the nicotine is tobacco-derived nicotine.

7. The oral product of claim 1, wherein the nicotine is synthetic nicotine.

8. The oral product of claim 1, further comprising an additive selected from the group consisting of minerals, vitamins, dietary supplements, nutraceuticals, energizing agents, soothing agents, amino acids, chemsthetic agents, antioxidants, botanicals, teeth whitening agents, therapeutic agents, and combinations thereof, wherein the additive is dispersed in the body such that the additive is released when the body is held within a mouth of an adult consumer.

9. The oral product of claim 1, further comprising a flavorant dispersed in the body such that the flavorant is released when the body is held within a mouth of an adult consumer, wherein the flavorant is selected from the group consisting of licorice, wintergreen, cherry and berry type flavorants, Dramboui, bourbon, scotch, whiskey, spearmint, peppermint, lavender, cinnamon, cardamon, *apium* graveolents, clove, cascarilla, nutmeg, sandalwood, bergamot, geranium, honey essence, rose oil, vanilla, lemon oil, orange oil, Japanese mint, *cassia*, caraway, cognac, jasmin, chamomile, menthol, ylang ylang, sage, fennel, pimenta, ginger, anise, coriander, coffee, mint oils from a species of the genus *Mentha*, and combinations thereof.

10. The oral product of claim 1, wherein the nicotine is absorbed in a fiber-polymer matrix formed by the mouth-stable polymer matrix and the cellulosic fibers.

11. The oral product of claim 1, wherein the body is shield shaped, wherein the body has a diameter of between 5 mm and 25 mm and a thickness of between 1 mm and 10 mm.

12. The oral product of claim 1, wherein the body comprises between 0.1 mg and 6 mg nicotine.

13. The oral product of claim 1, wherein the body has a compressibility @ 250 N of less than 95%.

14. The oral product of claim 1, wherein the body has a compressibility @ 250 N of between 45% and 90%.

15. The oral product of claim 1, wherein the body has a compressibility @ 425 N of between 60% and 98%.

16. The oral product of claim 1, wherein the body has a percentage of springiness of at least 20%.

17. The oral product of claim 1, wherein the body has a percentage of springiness of between 75% and 90%.

18. The oral product of claim 1, further comprising an antioxidant.

19. The oral product of claim 18, wherein the oral product comprises between 0.01 weight percent and 5.0 weight percent antioxidant.

20. The oral product of claim 18, wherein the antioxidant is ascorbyl palmitate.

21. The oral product of claim 1, further comprising a soluble fiber.

22. An oral product, comprising a body that is wholly receivable in an oral cavity, the body comprising:
    a mouth-stable polymer matrix having a shore Hardness of 50D or softer, the oral product comprising at least 60 weight percent of one or more mouth-stable polymers;
    at least 10 weight percent of non-tobacco cellulosic fibers embedded in the mouth-stable polymer matrix, the cellulosic fibers comprising cellulose, the cellulosic fibers having an average fiber size of less than 200 micrometers; and nicotine or derivative thereof dispersed in the mouth-stable polymer matrix such that the nicotine or derivative thereof is released from the body when the body is received within the oral cavity and exposed to saliva, wherein the cellulosic fibers provide passages in the mouth-stable polymer matrix to pores retaining the nicotine or derivative thereof, the pores having diameters of between 20 and 60 microns and between 1 and 10 microns;

wherein the oral product is substantially free of tobacco plant tissue.

23. An oral product, comprising a body that is wholly receivable in an oral cavity, the body comprising:

a mouth-stable polymer matrix comprising polyurethane, the oral product comprising at least 60 weight percent of one or more mouth-stable polymers;

at least 10 weight percent of non-tobacco cellulosic fibers embedded in the mouth-stable polymer matrix, the cellulosic fibers comprising cellulose, the cellulosic fibers having an average fiber size of between 75 and 125 micrometers;

a therapeutic agent absorbed into the non-tobacco cellulosic fibers and the mouth-stable polymer matrix; and nicotine or derivative thereof dispersed in the mouth-stable polymer matrix such that the nicotine or derivative thereof is released from the body when the body is received within the oral cavity and exposed to saliva, wherein the cellulosic fibers provide passages in the mouth-stable polymer matrix to pores retaining the nicotine or derivative thereof, the pores having diameters of between 20 and 60 microns;

wherein the oral product is substantially free of tobacco plant tissue.

24. The oral product of claim 22, further comprising a plasticizer dispersed in the mouth-stable polymer matrix.

25. The oral product of claim 24, wherein the plasticizer is selected from the group consisting of propylene glycol, glycerin, vegetable oil, triglycerides, and combinations thereof.

26. The oral product of claim 22, further comprising a sweetener dispersed in the body.

27. The oral product of claim 26, wherein the sweetener is selected from the group consisting of saccharine, sucralose, aspartame, acesulfame potassium, and combinations thereof.

28. The oral product of claim 22, wherein the nicotine is tobacco-derived nicotine.

29. The oral product of claim 22, wherein the nicotine is synthetic nicotine.

30. The oral product of claim 22, further comprising an additive selected from the group consisting of minerals, vitamins, dietary supplements, nutraceuticals, energizing agents, soothing agents, amino acids, chemsthetic agents, antioxidants, botanicals, teeth whitening agents, therapeutic agents, and combinations thereof, wherein the additive is dispersed in the body such that the additive is released when the body is held within a mouth of an adult consumer.

31. The oral product of claim 22, further comprising a flavorant dispersed in the body such that the flavorant is released when the body is held within a mouth of an adult consumer, wherein the flavorant is selected from the group consisting of licorice, wintergreen, cherry and berry type flavorants, Dramboui, bourbon, scotch, whiskey, spearmint, peppermint, lavender, cinnamon, cardamon, *apium* graveolents, clove, cascarilla, nutmeg, sandalwood, bergamot, geranium, honey essence, rose oil, vanilla, lemon oil, orange oil, Japanese mint, *cassia*, caraway, cognac, jasmin, chamomile, menthol, ylang ylang, sage, fennel, pimenta, ginger, anise, coriander, coffee, mint oils from a species of the genus *Mentha*, and combinations thereof.

32. The oral product of claim 22, wherein the nicotine is absorbed in a fiber-polymer matrix formed by the mouth-stable polymer matrix and the cellulosic fibers.

33. The oral product of claim 22, wherein the body is shield shaped, wherein the body has a diameter of between 5 mm and 25 mm and a thickness of between 1 mm and 10 mm.

34. The oral product of claim 22, wherein the body comprises between 0.1 mg and 6 mg nicotine.

35. The oral product of claim 22, wherein the body has a compressibility @ 250 N of less than 95%.

36. The oral product of claim 22, wherein the body has a compressibility @ 250 N of between 45% and 90%.

37. The oral product of claim 22, wherein the body has a compressibility @ 425 N of between 60% and 98%.

38. The oral product of claim 22, wherein the body has a percentage of springiness of at least 20%.

39. The oral product of claim 22, wherein the body has a percentage of springiness of between 75% and 90%.

40. The oral product of claim 22, further comprising an antioxidant.

41. The oral product of claim 40, wherein the oral product comprises between 0.01 weight percent and 5.0 weight percent antioxidant.

42. The oral product of claim 40, wherein the antioxidant is ascorbyl palmitate.

43. The oral product of claim 22, further comprising a soluble fiber.

44. The oral product of claim 23, further comprising a plasticizer dispersed in the mouth-stable polymer matrix.

45. The oral product of claim 44, wherein the plasticizer is selected from the group consisting of propylene glycol, glycerin, vegetable oil, triglycerides, and combinations thereof.

46. The oral product of claim 23, further comprising a sweetener dispersed in the body.

47. The oral product of claim 46, wherein the sweetener is selected from the group consisting of saccharine, sucralose, aspartame, acesulfame potassium, and combinations thereof.

48. The oral product of claim 23, wherein the nicotine is tobacco-derived nicotine.

49. The oral product of claim 23, wherein the nicotine is synthetic nicotine.

50. The oral product of claim 23, further comprising an additive selected from the group consisting of minerals, vitamins, dietary supplements, nutraceuticals, energizing agents, soothing agents, amino acids, chemsthetic agents, antioxidants, botanicals, teeth whitening agents, therapeutic agents, and combinations thereof, wherein the additive is dispersed in the body such that the additive is released when the body is held within a mouth of an adult consumer.

51. The oral product of claim 23, further comprising a flavorant dispersed in the body such that the flavorant is released when the body is held within a mouth of an adult consumer, wherein the flavorant is selected from the group consisting of licorice, wintergreen, cherry and berry type flavorants, Dramboui, bourbon, scotch, whiskey, spearmint, peppermint, lavender, cinnamon, cardamon, *apium* graveolents, clove, cascarilla, nutmeg, sandalwood, bergamot, geranium, honey essence, rose oil, vanilla, lemon oil, orange oil, Japanese mint, *cassia*, caraway, cognac, jasmin, chamomile, menthol, ylang ylang, sage, fennel, pimenta, ginger, anise, coriander, coffee, mint oils from a species of the genus *Mentha*, and combinations thereof.

52. The oral product of claim 23, wherein the nicotine is absorbed in a fiber-polymer matrix formed by the mouth-stable polymer matrix and the cellulosic fibers.

53. The oral product of claim 23, wherein the body is shield shaped, wherein the body has a diameter of between 5 mm and 25 mm and a thickness of between 1 mm and 10 mm.

54. The oral product of claim 23, wherein the body comprises between 0.1 mg and 6 mg nicotine.

55. The oral product of claim 23, wherein the body has a compressibility @ 250 N of less than 95%.

56. The oral product of claim 23, wherein the body has a compressibility @ 250 N of between 45% and 90%.

57. The oral product of claim 23, wherein the body has a compressibility @ 425 N of between 60% and 98%.

58. The oral product of claim 23, wherein the body has a percentage of springiness of at least 20%.

59. The oral product of claim 23, wherein the body has a percentage of springiness of between 75% and 90%.

60. The oral product of claim 23, further comprising an antioxidant.

61. The oral product of claim 60, wherein the oral product comprises between 0.01 weight percent and 5.0 weight percent antioxidant.

62. The oral product of claim 60, wherein the antioxidant is ascorbyl palmitate.

63. The oral product of claim 23, further comprising a soluble fiber.

\* \* \* \* \*